United States Patent
Rao et al.

(10) Patent No.: US 12,128,027 B2
(45) Date of Patent: Oct. 29, 2024

(54) N—N-DIMETHYLTRYPTAMINE (DMT) AND DMT ANALOG COMPOSITIONS, METHODS OF MAKING, AND METHODS OF USE THEREOF

(71) Applicant: ATAI Therapeutics, Inc., New York, NY (US)

(72) Inventors: Srinivas G. Rao, Encinitas, CA (US); Glen Short, Scituate, MA (US); Majed Fawaz, Foxboro, MA (US); Prerak Patel, Flemington, NJ (US); Santnu Patel, Ruppur (IN)

(73) Assignee: ATAI Therapeutics, Inc., New York, NY (US)

( * ) Notice: Subject to any disclaimer, the term of this patent is extended or adjusted under 35 U.S.C. 154(b) by 0 days.

(21) Appl. No.: 18/120,033

(22) Filed: Mar. 10, 2023

(65) Prior Publication Data

US 2023/0321039 A1    Oct. 12, 2023

Related U.S. Application Data

(63) Continuation of application No. 17/974,443, filed on Oct. 26, 2022, which is a continuation-in-part of application No. 17/730,013, filed on Apr. 26, 2022, now Pat. No. 11,602,521.

(60) Provisional application No. 63/179,679, filed on Apr. 26, 2021.

(51) Int. Cl.
| | |
|---|---|
| *A61K 31/4045* | (2006.01) |
| *A61K 9/00* | (2006.01) |
| *A61K 9/70* | (2006.01) |
| *A61K 47/10* | (2017.01) |
| *A61K 47/12* | (2006.01) |
| *A61K 47/26* | (2006.01) |
| *A61K 47/32* | (2006.01) |

(Continued)

(52) U.S. Cl.
CPC .......... *A61K 31/4045* (2013.01); *A61K 9/006* (2013.01); *A61K 9/7007* (2013.01); *A61K 47/10* (2013.01); *A61K 47/12* (2013.01); *A61K 47/26* (2013.01); *A61K 47/32* (2013.01); *A61K 47/38* (2013.01); *A61K 47/42* (2013.01)

(58) Field of Classification Search
CPC .. A61K 31/4045; A61K 9/006; A61K 9/7007; A61K 47/10; A61K 47/12; A61K 47/26; A61K 47/32; A61K 47/38; A61K 47/42
USPC .......................................... 424/435; 514/415
See application file for complete search history.

(56) References Cited

U.S. PATENT DOCUMENTS

| | | |
|---|---|---|
| 2020/0390746 A1 | 12/2020 | Rands et al. |
| 2020/0397752 A1 | 12/2020 | Castillo et al. |
| 2021/0015738 A1 | 1/2021 | LaRosa et al. |

(Continued)

OTHER PUBLICATIONS

Berge et al., "Pharmaceutical Salts," Journal of Pharmaceutical Science, Jan. 1977, pp. 1-19.

(Continued)

*Primary Examiner* — Taylor V Oh

(57) ABSTRACT

Pharmaceutical compositions including an amorphous N—N-dimethyltryptamine (DMT) or a pharmaceutically acceptable salt or prodrug thereof, and a polymeric carrier are described. These compositions are suitable for buccal or sublingual administration to a patient. Methods of treating disorders, including neurological disorders, by administration of these compositions are described.

20 Claims, 18 Drawing Sheets

(51) Int. Cl.
A61K 47/38 (2006.01)
A61K 47/42 (2017.01)

(56) References Cited

U.S. PATENT DOCUMENTS

| | | |
|---|---|---|
| 2021/0322306 A1 | 10/2021 | Espinoza et al. |
| 2021/0346347 A1 | 11/2021 | Witowski et al. |
| 2021/0378969 A1 | 12/2021 | Rands et al. |
| 2022/0031662 A1 | 2/2022 | Terwey |
| 2022/0061242 A1 | 3/2022 | Sperry et al. |
| 2022/0071958 A1 | 3/2022 | Terwey |
| 2022/0079881 A1 | 3/2022 | Modi |
| 2022/0304980 A1 | 9/2022 | Arnold et al. |
| 2023/0136824 A1* | 5/2023 | Rao .................. A61K 31/4045 424/435 |

OTHER PUBLICATIONS

Ruiz et al., Routes of Drug Administrations: Dosage Design, and Pharmacotherapy Sucess, Routes of Drug Administration, Chapter 6, Jan. 2018, pp. 1-43.
Strassman, Dose-Response Study of N, N-Dimethyltryptamine, in HumansArchives of General Psychiatry, Mar. 1994, pp. 85-97.

* cited by examiner

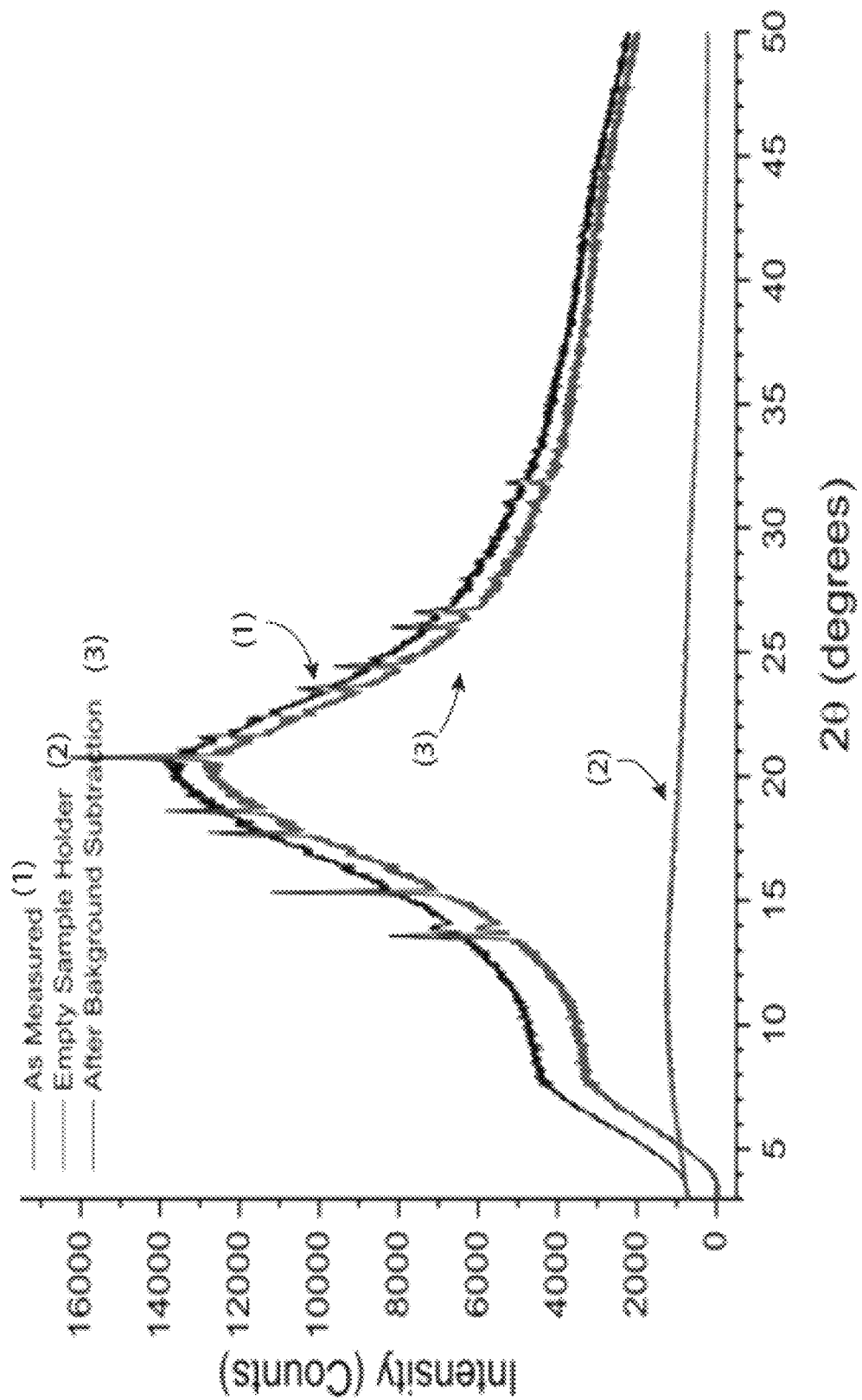
FIG. 2 (Formulation 23)

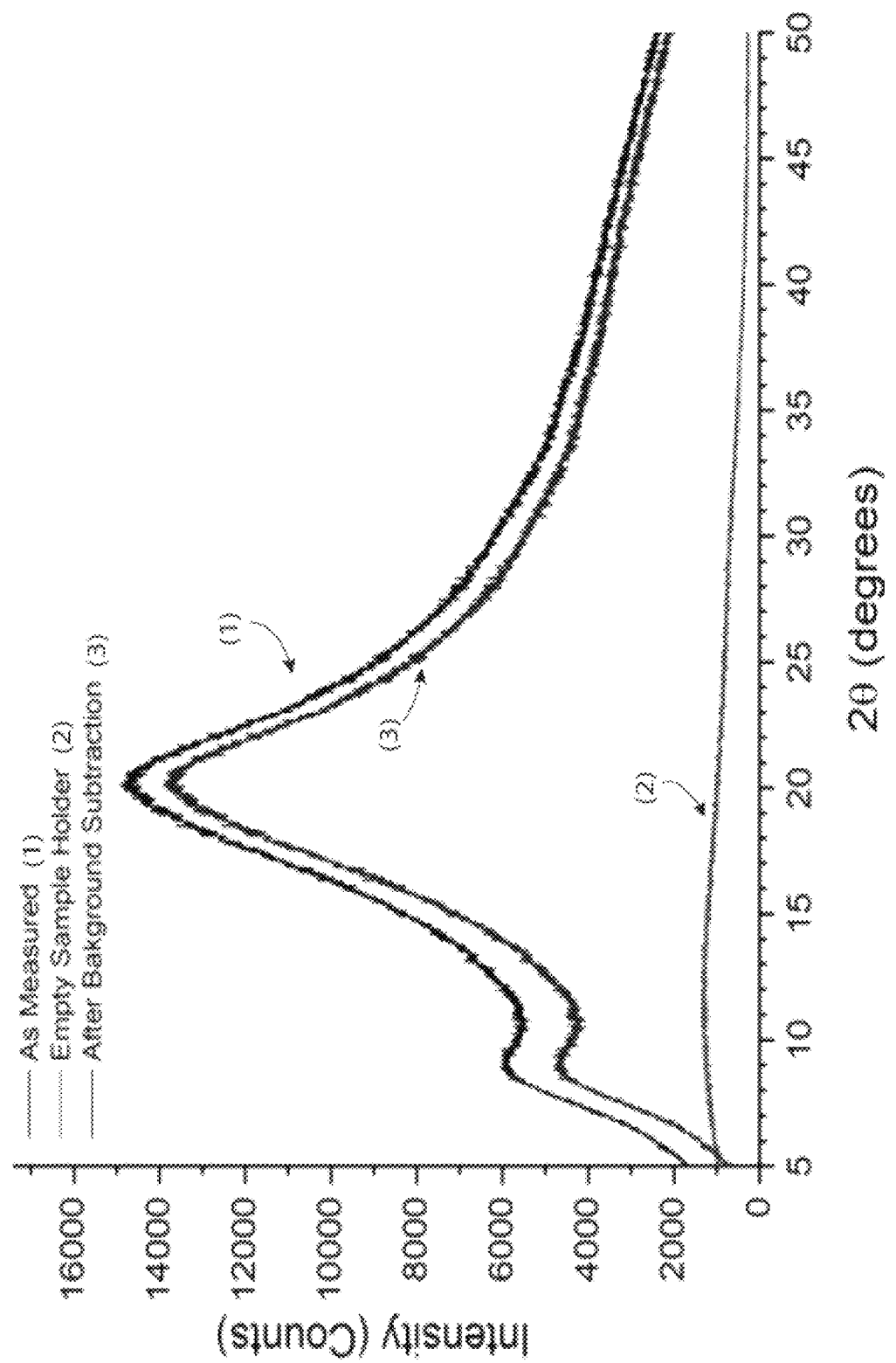

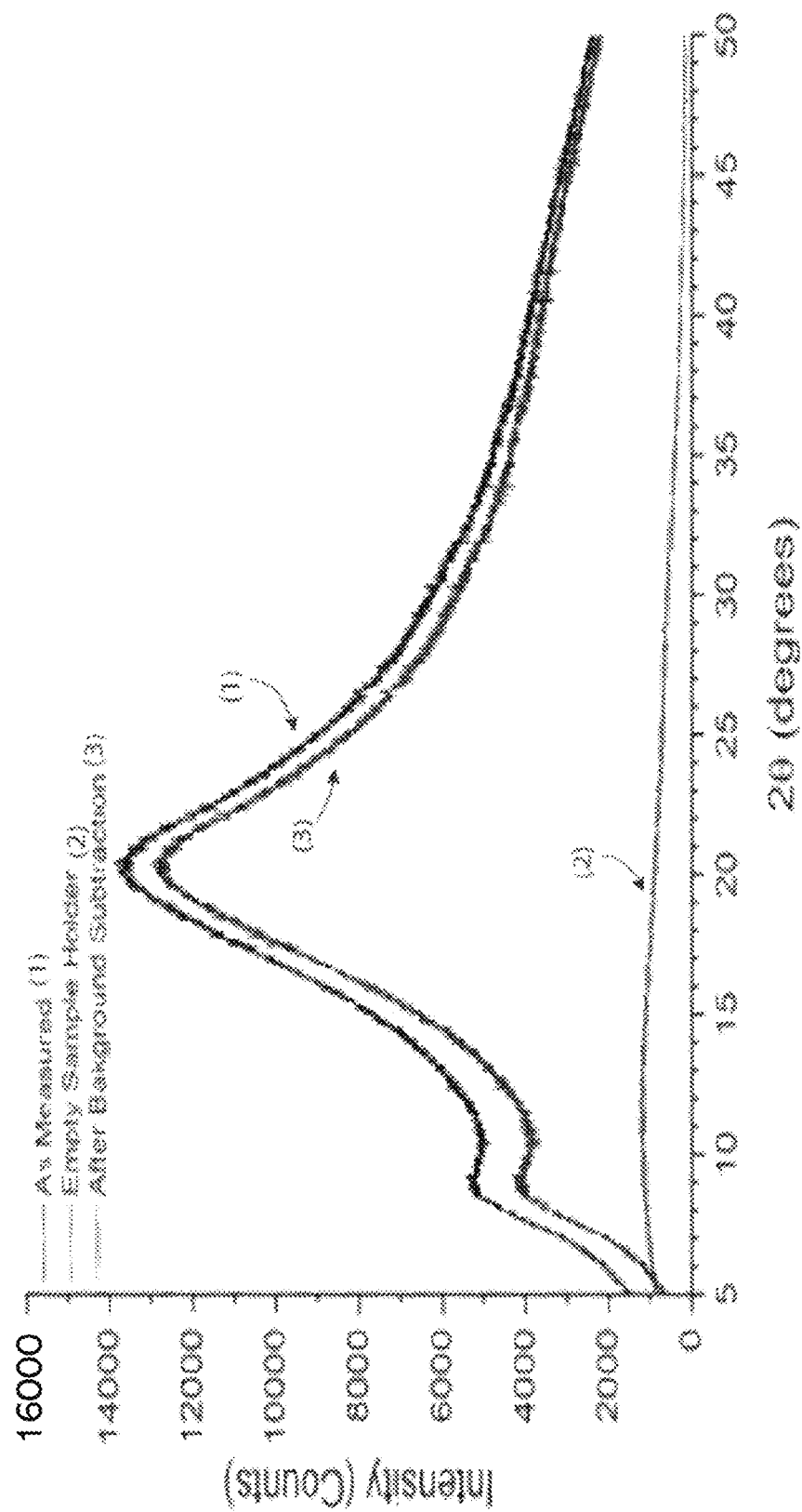
FIG. 3B (Formulation 24)

N—N-DIMETHYLTRYPTAMINE (DMT) AND DMT ANALOG COMPOSITIONS, METHODS OF MAKING, AND METHODS OF USE THEREOF

FIELD OF THE INVENTION

The present disclosure relates to novel N,N-dimethyltryptamine (hereinafter "DMT") compositions and methods of treating neurological diseases and conditions. Specifically, the disclosure provides improved pharmaceutical compositions comprising DMT in a form that permits controlled transmucosal release of DMT suitable for treatment of neurological diseases and conditions.

BACKGROUND OF THE INVENTION

Lysergic acid diethylamide ("LSD"), psilocybin and DMT are serotonergic agents often referred to as "classical hallucinogens" or "psychedelics," and have the ability to induce qualitatively altered states of consciousness, such as euphoria, trance, transcendence of time and space, spiritual experiences, or dissolution of self-boundaries, while other effects such as sedation, narcosis, or excessive stimulation are only minimal. Chemically, serotonergic psychedelics are either phenylalkylamines or indoleamines, with the indoleamine class being divided into two subsets, ergolines and tryptamines.

Naturally occurring psychedelics, such as the DMT, which is contained in the South American shrub *Psychotria viridis*, psilocybin, which is contained in over 200 mushroom species, or mescaline, which is contained in the Peyote cactus of the American Southwest and Northern Mexico, have been used for centuries by indigenous cultures in ritualistic or sociocultural contexts, and in the context of religious sacraments. While an unspecific "healing" potential had been ascribed to the use of naturally occurring psychedelics in those settings, more scientific investigations into their potential therapeutic application for defined diseases had not been pursued until after the discovery of the synthetic ergoline lysergic acid diethylamide ("LSD") in 1943.

With emerging knowledge about the serotonin system and its role in brain function, researchers began to specify the molecular activity of psychedelic drugs. However, how that activity translated into the observed therapeutic effects in mental disorders was less clear. Two main concepts were proposed: The first concept was coined "psycholytic therapy" and it emphasized the ability of psychedelics given at low doses to facilitate the loosening of psychological defensive mechanisms, which in combination with psychotherapy allows a deep introspective insight and the revival of traumata and their subsequent catharsis. The basic mechanism considered in the psycholytic approach was therefore the activation and deepening of the concomitant psychotherapeutic process, and it required multiple drug and therapy sessions. The second concept was coined as "psychedelic therapy" and it emphasized the ability of psychedelics given at relatively high single doses to induce so called "peak psychedelic experiences." Peak experiences are predominantly characterized by the loss of judgment to time and space and the dissolution of ego boundaries, which often culminates in the experience of a blissful state and feelings of being a whole and harmonious existence in the cosmic unity. The basic mechanism considered in the psychedelic approach was therefore to produce a unique, overwhelming experience with an intuitive perception of psychological integration and harmony and subsequent self-improvements and enhanced joy in living and a sense of inner peace.

Although scientific research around the use of psychedelics for the treatment of mental disorders blossomed in the 1960s, there was also a rapidly growing recreational use of these substances, and soon psychedelics were depicted in the media as highly dangerous drugs of abuse. A perceived danger to the social order led to the passage of the United States Controlled Substances Act of 1970, under which LSD and other psychedelics were placed into the most restrictive category Schedule 1, which contains drugs deemed to have no medical use and a high potential for abuse. Very little progress was made regarding possible therapeutic uses of psychedelic drugs for the next 30 years.

Recently, interest in the field of psychedelic therapy has resurged, and classical psychedelics have shown preclinical and clinical promise in treating psychiatric disorders (Carhart-Harris and Goodwin, The Therapeutic Potential of Psychedelic Drugs: Past, Present and Future, Neuropsychopharmacology; 42, 2105-2113 (2017)). In particular, psilocybin has demonstrated significant improvement in a range of depression and anxiety rating scales in randomized double-blind studies (Griffiths et al., Psilocybin produces substantial and sustained decreases in depression and anxiety in patients with life-threatening cancer: a randomized double-blind trial, Journal of Psychopharmacology 30(12), 1181-1197 (2016)).

DMT is also understood to hold therapeutic value as a psychedelic, with efficacy trials ongoing to assess the effect of DMT or DMT fumarate administered intravenously to subjects with major depressive disorder ("MDD"). However, although the intrinsic properties of DMT make it an attractive possible medication, especially for neurological diseases and conditions, current therapeutic compositions and modes of administration complicate treatment and may not provide optimal therapeutic results. For example, when smoked or delivered intravenously, DMT has a very fast onset of action and a short duration of effect, which presents a challenge to determine a suitable administration regimen with appropriate dosage and frequency of administration of DMT to provide effective therapy for neurological diseases and conditions. This is especially true for neurological diseases and conditions which would benefit from the presence of therapeutic blood levels of DMT over a more extended period of time following administration than can be achieved with a single dose of DMT via injection or inhalation.

Therefore, a significant need exists for readily administrable medications of DMT to treat neurological diseases and conditions. Such medications, which maximize efficacy while enabling drug side effects to be effectively controlled, are of particular interest, especially if administrable via a convenient route, including self-administration.

Several attempts to develop psychedelic formulations using traditional polymeric formulations have been described. For example, U.S. Publication 2021/0015738, to La Rosa et al. entitled "Oral Dissolvable Film Containing Psychedelic Compound" discloses an oral dissolvable film with DMT to treat neurological conditions. The oral dissolvable film that includes: (a) plasticizer, (b) solvent, (c) sweetener, (d) flavoring agent, (e) binder, (f) coloring agent, (g) preservative, and (h) psychedelic compound selected from the group consisting of psilocybin, psilocin, baeocystin, mescaline, LSD, ketamine, salvinorin A, ibotenic acid, muscimol, DMT, MDMA, MDEA, MDA, and combinations thereof.

U.S. Publication No. 2021/0322306, to Espinoza, entitled "Oral Dissolvable Film With High Load of Polymeric Binder" discloses a composition comprising (a) a film matrix that includes one or more binders, wherein at least one binder is a polymeric binder having a glass transition temperature (Tg) of at least 45° C.; (b) solvent; (c) an active pharmaceutical ingredient (API); and (d) pharmaceutically acceptable excipient that includes at least one of a mucoadhesive polymer, plasticizer, filler, bulking agent, saliva stimulating agent, stabilizing and thickening agent, gelling agent, flavoring agent, taste masking agent, coloring agent, pigment, lubricant, release modifier, adjuvant, sweetening agent, solubilizer & emulsifier, fragrance, emulsifier, surfactant, pH adjusting agent, buffering agent, lipid, glidant, stabilizer, antioxidant, anti-tacking agent, humectant, and preservative.

The above publications did not study stability of the compositions disclosed therein. There remains a need for stable DMT compositions that are capable of providing controlled release of DMT, particularly for transmucosal delivery.

SUMMARY OF THE INVENTION

The present disclosure provides, in one respect, a pharmaceutical composition, comprising an amorphous DMT or a pharmaceutically acceptable salt or prodrug thereof, and a polymeric carrier. The amorphous DMT may be characterized by a powder x-ray diffractogram free of any discernable peaks and differential scanning calorimetry (DSC) spectra for absence of sharp melting endotherm of crystalline DMT and/or indication of phase change (e.g., glass transition temperature). Stability may be characterized by observing these features over time, particularly after accelerated aging. The present inventors have unexpectedly found that DMT may be stabilized in an amorphous form within a polymeric carrier that is suitable for controlled transmucosal release of DMT. The stable amorphous DMT compositions may be provided in a form suitable for therapeutic transmucosal administration, e.g., buccal, or sublingual films.

The carrier may be a mucoadhesive polymer matrix. In some embodiments, the carrier matrix may comprise a cellulose derivative, a polyacrylic acid, a polyacrylate, a polyethylene oxide, polyvinyl pyrrolidone, polyvinyl alcohol, poly(vinyl pyrrolidone-co-vinyl acetate), hydroxypropyl cellulose, hydroxypropyl methyl cellulose, propylene glycol alginate ester, tragacanth, alginate, a gum, a soluble starch, gelatin, lectin, pectin, or chitosan, or a mixture thereof.

In some embodiments, the composition may include a permeation enhancer, a buffering agent, and a saliva stimulating agent. The permeation enhancer may include a bile salt, cetylpyridinium chloride (CPC), sodium lauryl sulfate (SLS), Tween 80, L-menthol, dimethyl sulfoxide (DMSO), oleic alcohol, oleic acid, oleyl oleate, levulinic acid, propylene glycol, dipropylene glycol, or ethanol, or a mixture thereof. The buffering agent may be citric acid, tartaric acid, fumaric acid, sodium citrate, sodium tartrate, or sodium fumarate, or a mixture thereof. The saliva stimulating agent may be citric acid, malic acid, lactic acid, ascorbic acid or tartaric acid, or a mixture thereof.

In some embodiments, the pharmaceutical composition may also include a stability enhancer, wherein the stability enhancer is an antioxidant or chelator. The stability enhancer may be α-tocopherol, tocopherol acetate, L-Glutathione, L-cysteine, ascorbic acid, ascorbyl palmitate, propyl gallate, butylated hydroxytoluene (BHT), butylated hydroxyanisole (BHA), Tocobiol or Ethylenediaminetetraacetic acid (EDTA), or a mixture thereof.

The composition may further comprise about 0% to about 10%, or about 0.1% to about 10% by weight of the buffering agent, about 2% to about 9% by weight of the buffering agent, or about 3% to about 8.5% by weight of the buffering agent.

The composition may further comprise about 0.1% to about 5% by weight of an antioxidant.

The composition may further comprise about 0% to about 8%, or about 0.1% to about 8% by weight of a saliva-stimulating agent.

In some embodiments, the pharmaceutical composition may further include hydrophilic adjuvants/additives or matrix solubilizing agent to promote water ingress and impacts film disintegration. It may include cellulose derivative, starch derivatives, cross linked povidone, cross linked cellulose, cross linked starch or alginates, sucrose, maltose, maltodextrin, isomaltose, ascorbic acids, acids, acid salts, sugar alcohols or a mixture thereof.

The composition may further comprise about 0% to about 15% by weight of a hydrophilic adjuvants/additives or matrix solubilizing agent.

In some embodiments, the pharmaceutical composition may further include a plasticizer, wherein the plasticizer is a polyethylene glycol (PEG), propylene glycol, glycerol, triacetin, or castor oil, or a mixture thereof.

In some embodiments, the pharmaceutical composition may further include a natural and/or artificial sweetener and/or flavoring agent. The sweetener may include sucrose, dextrose, fructose, glucose, maltose, maltitol, saccharin, sucralose, neotame, cyclamate, aspartame or acesulfame-K, or a mixture thereof. The flavoring agent comprises natural and/or synthetic flavor oils, oleoresins, and extract obtained from multiple parts of the plants such as leaves, fruits, flowers etc. The flavoring agent may include peppermint oil, cinnamon oil, vanilla extract, menthol, L-menthol or a mixture thereof.

The composition may further comprise about 0% to about 10% by weight of a sweetener.

The composition may further comprise about 0% to about 5% by weight of a flavoring agent.

In some embodiments, the pharmaceutical composition may further include natural colors such as cochineal dye, carotene, annatto dye, caramel dye etc. or synthetic coloring agents such as D&C and FD&C red, yellow, green, blue, inorganic/mineral colors (iron oxide red, iron oxide yellow, titanium dioxide etc.) The coloring agent is used alone or in combination.

The composition may further comprise about 0% to about 5% by weight of a coloring agent/color.

In certain embodiments, the carrier may include hydroxypropyl cellulose, a copolymer of N-vinyl-2-pyrrolidone and vinyl acetate, and hydroxypropylmethylcellulose. The carrier may further comprise polyethylene glycol, L-glutathione, citric acid, sucralose, maltitol, and L-menthol.

In some embodiments, the pharmaceutical composition may comprise (1) about 0.5% to about 60% by weight of an amorphous N—N-dimethyltryptamine or a pharmaceutically acceptable salt or prodrug thereof, (2) about 15% to about 80% by weight of a mucoadhesive polymer matrix; and (3) about 0.1% to about 30% by weight of a permeation enhancer. The composition may comprise about 20% to about 35% by weight of the N—N-dimethyltryptamine or a pharmaceutically acceptable salt or prodrug thereof. The composition may comprise about 50% to about 60% by weight of the mucoadhesive polymer matrix. The composition may comprise about 0.5% to about 20% by weight of the plasticizer. The composition may comprise about 0.5% to about 5% by weight of the plasticizer. The composition may comprise, for example, a mucoadhesive polymer matrix that comprises hydroxypropyl cellulose, a copolymer of N-vinyl-2-pyrrolidone and vinyl acetate, and hydroxypropyl methylcellulose.

In some embodiments, the pharmaceutical composition may comprise N—N-dimethyltryptamine or a pharmaceutically acceptable salt or prodrug thereof that is capable of being substantially fully solubilized and released in less than 1 minute following administration of the composition to a patient in need thereof.

In some embodiments, the pharmaceutical composition may comprise N—N-dimethyltryptamine or a pharmaceutically acceptable salt or prodrug thereof that is capable of being substantially fully solubilized and released in greater than 1 minute and less than 20 minutes following administration of the composition to a patient in need thereof.

In some embodiments, the pharmaceutical composition may comprise N—N-dimethyltryptamine or a pharmaceutically acceptable salt or prodrug thereof that is capable of being substantially fully solubilized and released in greater than 20 minutes and less than 3 hours following administration of the composition to a patient in need thereof.

In some embodiments, the composition is an oral film. The oral film may have a film thickness that is about 0.05 mm to about 0.4 mm.

In some embodiments, the invention relates to a method of treating a mental health condition or disorder, comprising administering a therapeutically effective amount of a composition above, wherein the mental health condition or disorder is major depressive disorder.

In some embodiments, the invention relates to a method of making a pharmaceutical composition, comprising the steps of: (1) combining N—N-dimethyltryptamine or a pharmaceutically acceptable salt or prodrug thereof, and excipients in a solvent; (2) removing the solvent to provide a polymeric matrix comprising an amorphous N—N-dimethyltryptamine or a pharmaceutically acceptable salt or prodrug thereof. The solvent may comprise methanol or an organic solvent in water, which may for example include a methanol-water in a 0:100 or 100:0 ratio. The method may comprise casting the polymeric matrix by removing the solvent. The solvent may include any organic solvent with a boiling point lower than water.

BRIEF DESCRIPTION OF THE FIGURES

FIG. 2 shows a PXRD Spectra of DMT polymeric film Formulation 23 showing the presence of crystalline peaks indicative of DMT.

FIG. 3A shows PXRD Spectra of DMT polymeric film Formulation 22 showing the absence of crystalline peaks, including any peaks indicative of DMT.

FIG. 3B shows PXRD Spectra of DMT polymeric film Formulation 24 showing the absence of crystalline peaks, including any peaks indicative of DMT.

DETAILED DESCRIPTION

Figure 1:
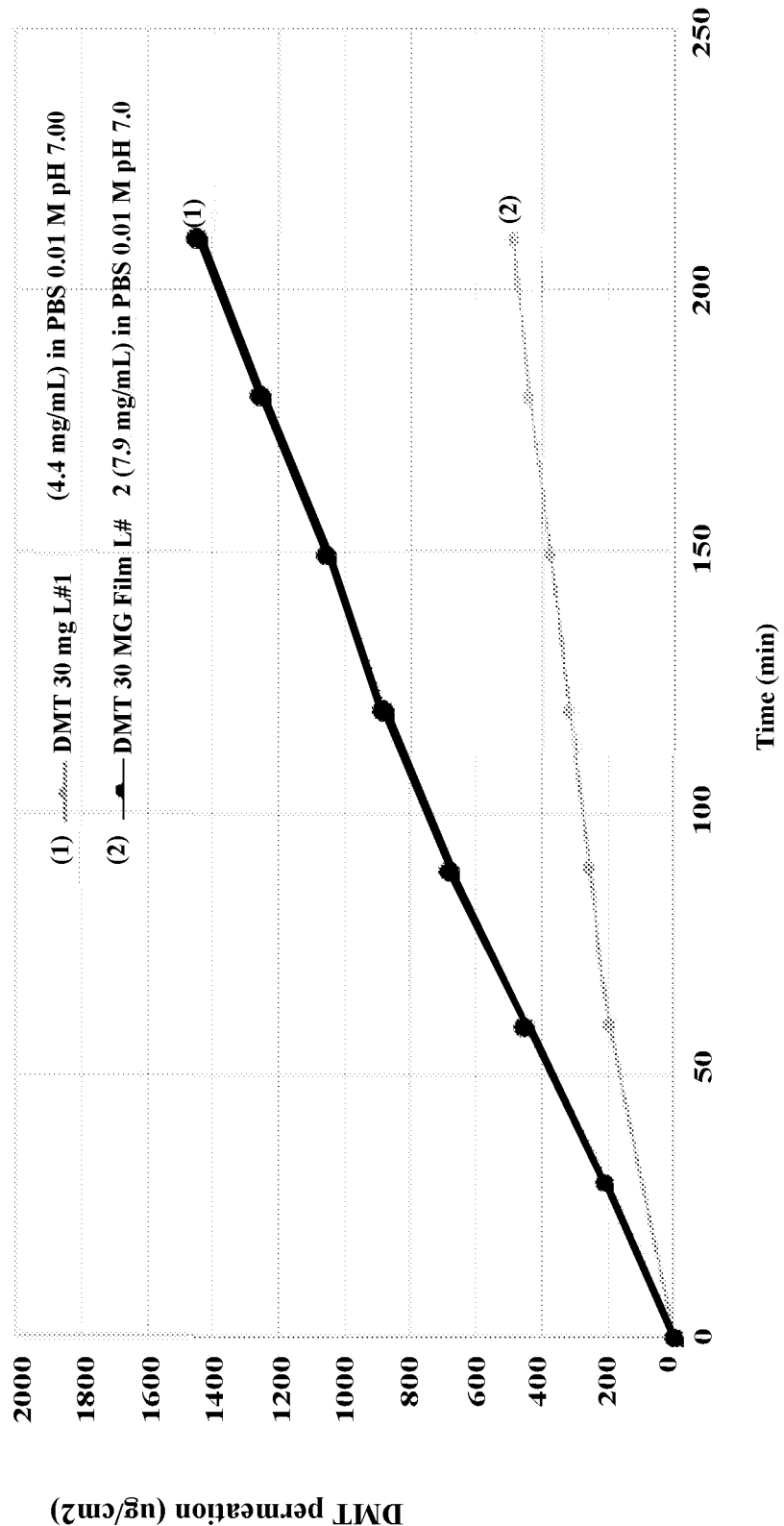
FIG. 1 shows permeability of DMT formulations (1) citric acid/citrate and (2) methanol/water through prepared films of porcine buccal mucosa.

The present invention relates to compositions of amorphous DMT which are capable of stabilizing DMT in amorphous form and providing controlled release of DMT in a suitable dosage form, for example, a transmucosal dosage form. The invention also relates to methods of making these amorphous DMT compositions, and methods of treatment of disease and disorders, e.g., neurological disorders, by administering these compositions to patients in need thereof.

Throughout this disclosure, various patents, patent applications and publications are referenced. The disclosures of these patents, patent applications and publications in their entireties are incorporated into this disclosure by reference for all purposes in order to describe the state of the art more fully as known to those skilled therein as of the date of this disclosure. This disclosure will govern in the instance that there is any inconsistency between the patents, patent applications and publications cited and this disclosure.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

The singular form "a", "an" and "the" include plural references unless the context clearly dictates otherwise. For example, the term "a pharmaceutically acceptable carrier"

may include a plurality of pharmaceutically acceptable carriers, including mixtures thereof.

The term "and/or" is intended to mean either or both of two components of the invention.

The term "subject," "individual" and "patient" are used interchangeably herein and refers to a human.

The term "carrier" refers to a diluent, adjuvant, excipient, or vehicle with which the therapeutic is administered and includes, but is not limited to, such liquids and powders that are hydrophilic substances, hydrophobic substances and substances that possess both hydrophilic and hydrophobic properties such as emulsifiers.

The term "device," as used herein, refers to an apparatus or system capable of delivering a drug to a patient in need thereof.

The terms "administer," "administering" or "administration" as used herein refer to administering a compound or pharmaceutically acceptable salt of the compound or a composition or formulation comprising the compound or pharmaceutically acceptable salt of the compound to a patient.

The term "in need of treatment" and the term "in need thereof" when referring to treatment are used interchangeably and refer to a judgment made by a caregiver (e.g., physician, nurse, nurse practitioner) that a patient will benefit from treatment.

The terms "treat" and "treatment" refer herein to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented. "Treatment" can, when concerning depression, also include reducing at least one sign or symptom of depression. Examples of a sign or symptom of depression include depressed mood, diminished interest in activities, weight loss or gain, decrease or increase in appetite, insomnia or hypersomnia, psychomotor agitation or retardation, fatigue or loss of energy, feelings of worthlessness or excessive or inappropriate guilt, diminished ability to concentrate or indecisiveness, or suicidal ideation or behavior.

The term "pharmaceutically acceptable" as used herein, refers to a component of a pharmaceutical composition that is compatible with the other ingredients of the formulation and not overly deleterious to the recipient thereof.

The term "effective amount" or "therapeutically effective amount" as used herein, refers to the amount of active agent that elicits the biological or medicinal response in a tissue, system, or individual that is being sought by a researcher, healthcare provider or individual.

The term "neurological disease or condition" as used herein, means a disease or condition selected from: a neuropsychiatric disorder, such as depression (including severe depression such as treatment-resistant depression, major depressive disorder and persistent depressive disorder), catatonic depression, a depressive disorder due to a medical condition, postpartum depression, premenstrual dysphoric disorder, or seasonal affective disorder, anxiety, anxiety disorder, social anxiety disorder, general anxiety disorder (GAD), avolition disorder, bipolar disorder (including bipolar I disorder and bipolar II disorder), post-traumatic stress disorder, body dysmorphic disorder, abnormalities of mood or emotion, including the above conditions, dysthymia, schizoaffective disorder, schizophrenia and other psychotic disorders, panic disorder, traumatic stress disorders, phobic disorders, and personality disorders with abnormal mood, such as borderline personality disorder, schizoid and schizotypal disorders and suicide ideation, or rumination/unproductive repetitive thoughts negatively impacting one's behavior/mood/ability to focus, obsessive-compulsive disorder, addiction (including substance use disorder such as addiction to nicotine, alcohol, cocaine, opioids, amphetamine, methamphetamine, heroin, morphine, phencyclidine, 3,4-methylenedioxy-methamphetamine, as well as other addictive substances), addictive behavior (including eating, gambling, sex, pornography, videogames, work, exercise, spiritual obsession, self-harm, travel and shopping addiction), eating disorder (including anorexia nervosa, bulimia nervosa and binge eating disorder), and pain (including pain associated with migraine or headache or chronic pain).

As used herein, the term "treatment-resistant depression" or "TRD" means a depressive disorder which does not respond satisfactorily to adequate treatment. TRD is a complex phenomenon influenced by variety in depressive subtypes, psychiatric comorbidity, and coexisting medical illnesses. Although TRD episodes are most commonly associated with major depressive disorder (MDD), they are also seen in the depressed phase of bipolar disorder.

As used herein, the term "onset" means the time to achieve maximum blood plasma concentration following administration (i.e., Tmax) and may also be described as "onset of action". A "rapid onset" in the context of the present disclosure means that the drug achieves $C_{max}$ within about 20 minutes (e.g., within about 2-10 minutes). However, onset following administration of a composition according to the present disclosure is less rapid, and consequently less "harsh" to the patient, than if DMT is administered by IV injection. In some cases, Tmax may be between 10 minutes and 90 minutes.

As used herein, the term "offset" means the time between the last time the concentration of DMT is at $C_{max} \pm 10\%$ and the first time the plasma concentration of DMT reduces to a threshold level below which the drug no longer has any meaningful therapeutic effect (e.g., about 250 nmol/L or 47.07 ng/mL). A "rapid offset" in the context of the present disclosure means less than about 10 minutes. However, although rapid, the offset is still sufficiently long for the drug to exert a reasonable duration of psychedelic effects.

The term "buccal delivery" or "buccal administration" refers to a route of administration in which the pharmaceutical dosage form is applied between the patient's cheek and gum (i.e., the buccal cavity).

The term "sublingual delivery" refers to a route of administration in which the pharmaceutical dosage form is applied under the patient's tongue.

The term "N, N-Dimethyltryptamine" or "DMT", includes the compound of formula (I):

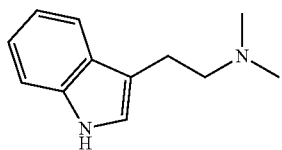 (I)

including pharmaceutically acceptable forms of DMT, including, but not limited to, salts, esters, polymorphs/solid state form, prodrugs. The term "DMT free form" or "DMT free base" refers to the compound of formula (I) without a pharmaceutically acceptable salt.

The term "pharmaceutically acceptable salt" as used herein with reference to "DMT or a pharmaceutically acceptable salt thereof" means a pharmaceutically acceptable acid addition salt. Typically, acidic reagents may be used to prepare salts, in particular pharmaceutically acceptable salts, of DMT. Examples of suitable acidic reagents include fumaric acid, hydrochloric acid, tartaric acid, citric acid, hydrobromic acid, sulfuric acid, succinic acid, phosphoric acid, acetic acid, maleic acid, lactic acid, tartaric acid and gluconic acid. Often, the form of the DMT salt in a pharmaceutical composition of the present disclosure or otherwise used according to the various aspects of the present disclosure, and embodiments thereof, is a pharmaceutically acceptable salt of a fumarate, hydrochloride, tartrate, succinate, or citrate salt, e.g., a fumarate salt.

The term "Amorphous", as used herein refers to a solid that is lacking the three-dimensional long-range order of a crystalline material, possess a more random arrangement of molecules, and have physical properties such as its solubility etc., quite different from those of their corresponding crystalline states.

The term "microenvironmental pH" also called "local pH" also called "surface pH" refers to the pH of the region of the carrier/polymeric matrix immediately surrounding the active agent as the matrix hydrates and/or dissolves, for example, in the mouth of the user. Buffering agent also influences the disintegration time of buccal film.

As used, herein, "transmucosal film" refers to polymeric film capable of embedding active ingredients which allows mucosal adhesion, complete solubilization or dissolution, diffusion and transmucosal delivery of active for systemic absorption.

The term "Transmucosal", as used herein, refer to any route of administration across the mucosal membrane. Examples include, but are not limited to, buccal, sublingual, gingival, on the tongue, nasal, vaginal, and rectal. In this embodiment, the administration route is buccal or sublingual.

The term "Mucoadhesion" refers to the phenomenon where polymers hydrates in presence of mucous fluid and adhere to the mucosal surface. Polymers that can readily form a gel in an aqueous environment can cause dehydration at the mucosal site of application. The water drawn into the film will help dissolving the active ingredient. Once the active ingredient is absorbed more water is absorbed by the remaining film due to a concentration gradient. This process leads to the mixture of formulation and mucus and can thus increase contact time with the mucous membrane. See, e.g., Mucoadhesive drug delivery systems, Flávia Chiva Carvalho, Marcos Luciano Bruschi, Raul Cesar Evangelista, Maria Palmira Daflon Gremião, BJPS, vol. 46, n. 1, January/March, 2010.

The term "Polymeric carrier matrix or mucoadhesive polymeric matrix" refers to a carrier comprising combination of polymers with different functional properties such as but not limited to mucoadhesion, stabilizing (chemical and physical stabilizer), gelling, film forming, release controlling, swelling etc.

Pharmaceutical Compositions and Delivery

The present invention in one aspect involves oral transmucosal formulations in which an active ingredient comprising DMT is released in a therapeutically effective manner.

DMT is a natural occurring molecule and is a known psychedelic drug with rapid onset and relatively short duration effect. DMT is not active upon oral administration and converts to inactive metabolites in gastrointestinal tract (GI) and liver before sufficient penetration to the brain can occur which results in low oral bioavailability. Hence, in the present invention, alternate route of administration such as oral transmucosal (e.g., buccal/sublingual/gingival/mucosal (on the oral mucosa) or on the tongue is explored to improve DMT bioavailability by circumventing GI and hepatic first pass metabolism. See Metabolism GAP Analysis of DMT Literature, Gina Patel, Mpharm, PhD, President and CEO, Patel Kwan Consultancy, 25 Aug. 2020.

DMT is believed to have good permeability across the biological membrane. However, DMT free form exhibited poor aqueous solubility and hence, from a buccal formulation permeability of DMT could be governed by the solubility of DMT at buccal mucosa. Hence, solubility enhancement of DMT at the site of absorption at buccal mucosa is required to achieve its bioavailability. Several approaches can be employed for solubility enhancement of DMT at buccal site such as employing, but not limited to, modifying physical form, salt, prodrug form of DMT, modification of microenvironmental pH, solubilizer, micronization, nanoparticles, emulsions etc. In one aspect of the present invention, buccal formulations are design with an objective to modify polymorphic form/solid state form, preferably to amorphous form, to improve its solubility and thus the overall permeability across the buccal mucosa to achieve desired pharmacokinetics.

DMT free base is a lipophilic molecule (log P–2.573) with a small backbone (Mol wt. 188.27 g/mol). The present inventors found that DMT may exist in several polymorph forms, including at least forms I-IV, with form IV of DMT being most stable among different forms studied. The present inventors also found that amorphous N,N-DMT exhibited a low glass transition temperature (−18° C.) and readily crystallizes, particularly at temperatures above the Tg. For this reason, DMT is expected to have insufficient stability to be reliably delivered to the patient in amorphous form without a stabilizer.

The present inventors have discovered that by controlling the conditions upon which DMT is incorporated into a polymeric film, it is possible to obtain a film that includes DMT in a stable amorphous form suitable for transmucosal administration. For example, the conditions to achieve a stable DMT-containing film may include use of particular solvents in particular amounts alone or in combination with modifying the pH of the composition. These conditions may be provided to solubilized DMT within a casting solution whereby the casting solution is molded into a suitable form, and evaporation of solvent leads to the creation of the polymeric film. Alternatively, or in addition, the process may include spray drying the polymer or stabilizer and DMT in a suitable solvent in order to incorporate DMT in a stable amorphous form. In some embodiments the resultant spray dried material may be directly incorporated into a polymeric film, or tablets or other suitable dosage forms.

As explained in further detail with respect to the examples of this application, appropriate control of pH and/or solvent conditions during formation of the DMT/polymer composition are important factors in achieving a stable amorphous DMT/polymer composition. The inventors have found that lowering pH of the DMT/polymer composition may result in ionization of the DMT molecule in a manner that could negatively impact transmucosal delivery. In this aspect, some combination of pH modulation and use of an appropriate solvent during DMT/polymer formation may be desirable in the preparation of a stable amorphous DMT/polymer composition.

The present invention, in one aspect, there contemplates incorporation of DMT into compositions and dosage forms, including but not limited to, fast dissolving tablets, microporous hollow fibers, chewing gum, tablets, fast or rapid disintegrating tablets, wafers, disks, powders, mucoadhesive gels, ointments, pastes, sponges, emulsions, single layer film, bilayer film, multilayered film, mouthwashes, aerosols, sprays, drops, gummies, bi-layer or multi-layer tablets, mucoadhesive tablets etc. In one embodiment, preferred formulation is a buccal/sublingual film. These films may be divided in three main categories depending on the time for dissolution in the oral cavity. Quick Release (QR) film which solubilizes within seconds, generally less than a minute, other is moderate releasing film, which takes a few minutes to up to 20 minutes, and sustained release (SR) film, which solubilizes at a slower rate than moderate releasing film and takes more than 20 min to up to few hours.

QR films release active in the oral cavity in seconds and offer less or no contact time with buccal or sublingual mucosa. However, moderate release or SR films offer longer contact time at the mucosal surface which increases the chance of the active ingredient to be directly absorbed through mucosa. Pharmaceutical compositions comprising amorphous DMT or a pharmaceutically acceptable salt thereof suitable for buccal and sublingual administration include rapidly dissolving tablets, wafers, films, strips or patches, orodispersible tablets, oral gels, medicated lollipops, sprays, drops, gummies and other formulations that are retained on the buccal or sublingual mucosal surface.

In some embodiments, the examples of buccal/sublingual films include a rapid/quick release film (simply QR film) and moderate release composition comprising the drug present as a solid solution or a suspension form or a partially soluble form in a mucoadhesive polymeric carrier matrix, where upon administration of film in the oral cavity, the film disintegrates in a specified time to release drug and make it available for absorption through oral mucosa. QR films and moderate release films are designed to provide instantaneous release of the active ingredient after administration.

The present invention contemplates in one aspect, an amorphous DMT/polymer composition that includes one or more of matrix polymer or mucoadhesive polymer, permeation enhancer, plasticizer, antioxidant, buffering agent, and optionally sweetening agent, saliva stimulating agent, coloring agent, hydrophilic adjuvant/additive and/or flavoring agent.

Suitable mucoadhesive polymers include one or more polymers selected from cellulose derivatives, polyacrylic acids, polyacrylates, polyethylene oxides, polyvinyl pyrrolidones, poly(vinyl pyrrolidone-co-vinyl acetate), polyvinyl alcohols, propylene glycol alginate esters, tragacanth, alginates, gum (including karaya gum, guar gum, xanthan gum), soluble starch, gelatin, lectin, pectin, and chitosan. In some embodiments, the mucoadhesive polymer comprises one or more polymers selected from a hydrophilic polymer, a polysaccharide and its derivatives, and a hydrogel. In some embodiments, the mucoadhesive polymer comprises one or more polymers selected from polyacrylic acids, polyacrylates, celluloses, e.g., carboxycelluloses (e.g., sodium carboxymethyl cellulose), hydroxyalkyl cellulose (e.g., hydroxypropylcellulose, hydroxyethylcellulose and hydroxyethyl ethyl cellulose), polyvinylpyrrolidone, poly (vinyl pyrrolidone-co-vinyl acetate) and polyvinyl alcohol. In some embodiments, the mucoadhesive polymer comprises one or more polymers selected from Carbopol (polyacrylic acid), carboxymethyl cellulose, carboxyethyl cellulose, hydroxypropyl cellulose, hydroxypropylmethyl cellulose, and gum. In some embodiment, the mucoadhesion is attributed to material containing thiol group such as but not limited to, N-acetyl cysteine, glutathione, thiolated polycarbophil (a copolymer of acrylic acid and divinyl glycol), thiolated chitosan, thiolated sodium carboxymethylcellulose, thiolated sodium alginate, thiolated sodium hydroxypropyl cellulose, thiolated hyaluronic acid and thiolated pectin. See, e.g., Thiolation of Biopolymers for Developing Drug Delivery Systems with Enhanced Mechanical and Mucoadhesive Properties: A Review, Vivek Puri, Ameya Sharma, Pradeep Kumar, Inderbir Singh. Polymers 2020, 12, 1803; doi:10.3390/polym12081803. In some embodiments, the mucoadhesive polymer is water-swellable. Typically, the mucoadhesive polymer is present alone or in combination in a total amount of about 15% to about 80% by weight of the film composition.

The film compositions can further include a permeation enhancer. For example, in some embodiments, the film composition comprises a permeation enhancer, e.g., comprising one or more permeation enhancers selected from bile salts such as sodium deoxycholate (SDC), including sodium glycodeoxycholate (SGDC), sodium taurodeoxycholate (STDC) and others; synthetic surfactants such as Cetylpyridinium chloride (CPC), Sodium lauryl sulfate (SLS) Tween 80 and others but not limited to L-menthol, dimethyl sulfoxide (DMSO), oleic alcohol, oleic acid, oleyl oleate, levulinic acid, propylene glycol, dipropylene glycol, ethanol, and surfactants. In some embodiments, the permeation enhancer is present in an amount of about 0.1% to about 30% by weight of the film composition.

In some embodiments, the film composition can further include an antioxidant, e.g., comprising one or more antioxidants such as α-tocopherol, tocopherol acetate, L-Glutathione, L cysteine, ascorbic acid, ascorbyl palmitate, propyl gallate, butylated hydroxytoluene (BHT), butylated hydroxyanisole (BHA), Tocobiol and Ethylenediaminetetraacetic acid (EDTA). In some embodiments, the antioxidant is present in an amount of about 0.1% to about 5% by weight of the film composition.

The film compositions can further include plasticizer. A plasticizer improves the flexibility of the film and reduces the brittleness of the film by reducing the glass transition temperature of the film. For example, in some embodiments, the film composition comprises plasticizer e.g., comprising one or more plasticizers selected from but not limited to polyethylene glycols (PEGs) such as PEG 300, PEG 400 etc.; propylene glycol, glycerol, triacetin, castor oil. In some embodiments, the plasticizer is present in an amount of about 0.5% to about 20% by weight of the film composition.

The film compositions can further include sweetening agent to improve the taste. The stimulation of saliva production increases the saliva production that would aid in faster solubilization of film and active for faster absorption.

In some of the examples natural or artificial sweeteners, are used to improve the palatability of the formulation. For example, in some embodiments, the film composition comprises sweetener e.g., comprising one or more selected from but not limited to sucrose, dextrose, fructose, glucose, liquid glucose, maltose, maltitol, saccharin, sucralose, neotame, cyclamate, aspartame and acesulfame-K etc. In some embodiments, the sweetner is present in an amount of about 0% to about 10% by weight of the film composition.

The film compositions can further include a saliva stimulating agent. In some of the examples, citric acid, malic acid, lactic acid, ascorbic acid, succinic acid, fumaric acid and tartaric acid are used as salivary stimulants. Stimulating agents are used alone or in combination between about 0% to about 8% or about 0.1 to about 8% w/w of weight of the dry film composition.

The film composition can further include a flavoring agent. In some examples natural and/or synthetic flavor oils, oleoresins, and extract obtained from multiple parts of the plants such as leaves, fruits, flowers etc. such as peppermint oil, cinnamon oil, vanilla extract, menthol, L-menthol or a mixture thereof are used as flavoring agent. In some embodiments, the flavoring agent is present in an amount of about 0% to about 5% by weight of the film composition.

The film composition can further include hydrophilic adjuvants/additives or matrix solubilizing agent to promote water ingress and impacts film disintegration. In some of the examples cellulose derivative, starch derivatives, cross linked povidone, cross linked cellulose, cross linked starch or alginates, sucrose, maltose, maltodextrin, isomaltose, ascorbic acids, acids, acid salts, sugar alcohols or a mixture thereof are used as hydrophilic adjuvants/additives or matrix solubilizing agent. In some embodiments, the hydrophilic adjuvants/additives or matrix solubilizing agent is present in an amount of about 0% to about 15% by weight of the film composition.

The film composition can further include natural colors such as cochineal dye, carotene, annatto dye, caramel dye etc. or synthetic coloring agents such as D&C and FD&C red, yellow, green, blue, inorganic/mineral colors (iron oxide red, iron oxide yellow, titanium dioxide etc.) The coloring agent is used alone or in combination. In some embodiments, the coloring agent is present in an amount of about 0% to about 5% by weight of the film composition.

DMT is weak base with pKa of 8.86. The pH of the film plays a very important role in balancing its ionized vs unionized form at the site. In the present invention microenvironmental pH is maintained to achieve balance between ionized and unionized form and thus the permeation across the mucosa.

In one aspect, the polymeric film surface pH/diffusion environment, also called microenvironmental pH, may be maintained to desired pH close to physiological pH of saliva. The microenvironmental pH can be adjusted and/or maintained by adjusting polymeric film pH utilizing methods including, but not limited to, the use of acid, base, buffering agent in the formulation.

The film composition can include acid, base or buffering agent which could influence the pH and help maintain desired microenvironmental pH at the site of application in the oral cavity. In some embodiments, the film composition comprises of acid, base or buffering agent, not limited to, citric acid, tartaric acid, fumaric acid, sodium citrate, sodium, tartrate, sodium fumarate etc. Buffering agent are used alone or in combination between about 0% to about 10% or about 0.1 to about 10% w/w of the film composition.

Additionally, a inactive backing layer may be added on top of the active film to make it bilayer film in order to reduce or prevent erosion from the back side of the film when applied to the mucosal surface. Backing layer may further help to improve taste of the film.

The amount of active e.g., DMT or its suitable form, to be incorporated into the polymeric film depends on the desired dosage to be administered. For example, DMT or its suitable form can be present in about 0.5% to about 60% by weight of film.

One additional benefit of buccal or sublingual film is that less dose is required to achieve desired bioavailability in contrast to an oral dose which needs co-administration of monoamine oxidase inhibitors to achieve DMT oral bioavailability. See, e.g., N, N-Dimethyltryptamine (DMT), an Endogenous Hallucinogen: Past, Present, and Future Research to Determine Its Role and Function. Steven A. Barker, Front. Neurosci., 6 Aug. 2018 https://doi.org/10.3389/fnins.2018.00536.

In some embodiments, buccal or sublingual films were prepared with a thickness range from about 0.01 mm to about 1.5 mm, and more specifically from about 0.05 to about 0.4 mm. Further, the thickness of the film could be varied from 10% to 90% to these ranges based on the drug-polymeric mixture.

The prepared films were evaluated for physicochemical properties such as appearance, disintegration time, dissolution, assay, water content, degradation products, polymorphic form evaluation, mechanical properties such as folding endurance, elongation, tensile strength etc. and ex-vivo permeability through porcine buccal mucosa or permeapad membrane.

DMT Solubility Evaluation

Solubility studies of DMT have been carried out in various solvents by preparing super saturated mixture and analyzed using HPLC. The results shown below.

Results of DMT solubilization with different solvents is shown in Table 1.

TABLE 1

| Solvent | Solubility (mg/mL) |
| --- | --- |
| Acetone | >126 |
| Tetrahydrofuran | >106 |
| p-dioxane | >104 |
| Ethanol | >98 |
| Methanol | >98 |
| Acetonitrile | >94 |
| Methyl isobutyl ketone | >90 |
| Isopropyl Alcohol Water | >98 |
| Water | <1 |
| Saliva Buffer (pH 6.8) | 2.3 |
| Methanol:Water (70:30) | >50 |
| Methanol:Water (50:50) | 26 |

The solubility study was performed on DMT API as is, the crystalline form, and the results showed poor water/aqueous solubility. This warrants a strong need for improvement solubility of DMT API in the film formulation for better bioavailability.

The present work also aims to convert API to its amorphous form to improve solubility and maintaining same form in the formulation throughout the shelf life. Suitable methods of manufacturing has been chosen to convert DMT into amorphous form and various combinations of polymers have been incorporated in the formulation to stabilize the amorphous form in the film during the shelf life. The choice of polymers includes one or more polymers selected from cellulose derivatives, polyacrylic acids, polyacrylates, polyethylene oxides, polyvinyl pyrrolidones, poly(vinyl pyrrolidone-co-vinyl acetate), polyvinyl alcohols, propylene glycol alginate esters, tragacanth, alginates, gum (including karaya gum, guar gum, xanthan gum), soluble starch, gelatin, lectin, pectin, and chitosan. In some embodiments, the polymer comprises one or more polymers selected from a hydrophilic polymer, a polysaccharide and its derivatives, and a hydrogel. In some embodiments, the polymer comprises one or more polymers selected from polyacrylic acids, polyacrylates, celluloses, e.g., carboxycelluloses (e.g., sodium carboxymethyl cellulose), hydroxyalkyl cellulose (e.g., hydroxypropylcellulose, hydroxyethylcellulose and hydroxyethyl ethyl cellulose), polyvinylpyrrolidone, and polyvinyl alcohol. In some embodiments, the polymer comprises one or more polymers selected from Carbopol (polyacrylic acid), carboxymethyl cellulose, carboxyethyl cellulose, hydroxypropyl cellulose, hydroxypropylmethyl cellulose, and gum.

Further, several excipients for formulating transmucosal films with desired properties have been analyzed for compatibility with DMT at 50° C./75% RH utilizing HPLC method to detect impurity levels. The results are shown in Table 2 below.

TABLE 2

| Binary mixture | No. of Impurities | Total Impurities % |
|---|---|---|
| DMT | 6 | 2.17 |
| DMT + BHT | 3 | 1.33 |
| DMT + Citric Acid | 5 | 0.94 |
| DMT + NA Citrate anhydrous | 6 | 0.92 |
| DMT + Sucralose | 10 | 5.88 |
| DMT + Magnasweet | 9 | 2.60 |
| DMT + Advantame | 7 | 4.45 |
| DMT + L MENTHOL | 6 | 1.62 |
| DMT + Propylparaben | 9 | 4.94 |
| DMT + Maltitol | 6 | 2.86 |
| DMT + Na Bisulfite | 22 | 8.37 |
| DMT + Titanium Dioxide | 6 | 2.55 |
| DMT + Evospray nat lime | 9 | 4.52 |
| DMT + NA2EDTA-Dihydrate | 15 | 7.63 |
| DMT + Plasdone S630 | 5 | 2.30 |
| DMT + HPMC E50 | 6 | 1.90 |
| DMT + Pullulan | 8 | 3.54 |
| DMT + HPC SSL NISSO | 6 | 1.70 |
| DMT + PVP K90 | 10 | 3.86 |
| DMT + PEO WSR N80 | 6 | 2.12 |
| DMT + Xanthan Gum | 9 | 5.56 |
| DMT + CMC CEKOL 150 | 12 | 6.06 |
| DMT + Acacia Gum | 9 | 4.24 |
| DMT + MALTODEXTRIN M180 | 9 | 4.94 |
| DMT + Corn starch Purity 21C | 7 | 3.14 |
| DMT + HPC LF Klucel | 6 | 1.65 |
| DMT + PEG300 | 6 | 2.74 |
| DMT + Glycerol | 8 | 4.44 |
| DMT + tween 20 CRODA | 6 | 2.05 |
| DMT + OH SOY Lecithin | 7 | 3.81 |
| DMT + Sorbitol | 6 | 2.60 |
| DMT + Propylen Glycol | 6 | 2.41 |

A forced degradation study of DMT was performed under different stress conditions and samples are analyzed using HPLC. The results are shown in Table 3 below.

TABLE 3

| Condition (Exposure Overnight) | % Assay |
|---|---|
| 0.1N HCl | 99.7% |
| 0.1N NaOH | 99.4% |

TABLE 3-continued

| Condition (Exposure Overnight) | % Assay |
|---|---|
| 3% peroxide | 26.6% |
| 70° C. | 98.5% |

DMT has been shown to be highly prone to oxidation upon force degradation study as suggested by the data in the above table. It is important to incorporate antioxidant(s) in the formulation to prevent oxidation of DMT during the shelf life and to form stable films.

From solubility, forced degradation and compatibilities studies various functional and non-functional excipients have been selected along with several others for further studies.

Methods of DMT Film Manufacturing

Different manufacturing techniques such as solvent casting method, hot-melt extrusion, semisolid casting, solid dispersion extrusion, rolling method etc. can be used for DMT polymer formation, for example in the preparation of transmucosal (e.g., buccal, sublingual etc.) film manufacturing. The solvent casting method is the most preferred method for the manufacturing of buccal film and has been well studied in the past. The buccal film of DMT is manufactured using the solvent casting method. DMT as Form I (Investigations into the polymorphic properties of N,N-dimethyltryptamine by X-ray diffraction and differential scanning calorimetry, Gaujac et al (2013)) or Form IV and excipients are mixed with suitable solvent system to form a uniform mixture with DMT in solution form. The resulting mixture is subjected to deaeration, used to cast a film, allowed to dry to obtain films containing DMT as amorphous form. The films are then cut into strips of desired sizes to produce desired film strengths of DMT.

In present work the solvents have been selected to solubilize DMT completely in the mixture and upon casting and drying to evaporate solvent/s to form amorphous DMT in the polymer matrix. The well-known techniques like PXRD and DSC have been utilized to confirm the conversion to the amorphous form.

In some examples of present invention DMT alone and films containing DMT as amorphous and/or crystalline form have been prepared in combination with other excipients to achieve solubility and permeability.

Example 1

In an exemplary embodiment, DMT polymeric films were prepared according to the formula given in table 4 below.

TABLE 4

| | Formulation | |
|---|---|---|
| | 1 | 2 |
| Ingredients | Film Composition (% w/w) | |
| DMT | 12.99 | 21.11 |
| Citric Acid | 3.98 | — |
| Sodium citrate anhydrous | 4.55 | — |
| Propylene glycol | 1.74 | 8.861 |
| Sucralose | 0.87 | 0.800 |
| Povidone (PVP K-90) | 25.18 | 22.32 |

TABLE 4-continued

| Ingredients | Formulation 1 Film Composition (% w/w) | Formulation 2 Film Composition (% w/w) |
|---|---|---|
| HPC (Nisso HPC-L) | 50.26 | 44.644 |
| L-menthol | — | 1.849 |
| Methanol (% w/w solvent composition) | — | 70 |

TABLE 4-continued

| Ingredients | Formulation 1 Film Composition (% w/w) | Formulation 2 Film Composition (% w/w) |
|---|---|---|
| Water (% w/w solvent composition) | 100 (Water based formula in citrate buffer) | 30 |

The film using the above composition was prepared as follows: DMT and excipients were mixed with either water-based citrate buffer or methanol-water (70:30) solvent mix to form a homogenous mixture. The resulted mixture was de-aerated. The film was casted using a de-aerated mixture, dried and cut into strips.

Further, permeability of DMT through prepared films were evaluated using ex-vivo permeation study i.e., using porcine buccal mucosa as presented below. Ex-vivo permeation is well studied using Franz diffusion cell or Using chambers utilizing animal mucosa (e.g., Pig or sheep buccal mucosa) or by using commercially available synthetic membranes (e.g., Permeapad®). The Franz diffusion cell consists of two compartments; one is the donor compartment, the other is the receptor compartment of 18 mL capacity and having 0.785 cm$^2$ effective diffusion area. The temperature is maintained at 37° C. by water jacket. This technique can also establish good discrimination tool to optimize formulation composition to achieve desired permeability and determine time required for film to be retained at the buccal surface to offer desired rate and extent of DMT absorption. Films prepared using aqueous as well as hydroalcoholic mixture demonstrated permeability of DMT across the porcine buccal mucosa as shown in FIG. 1

Example 2

In an exemplary embodiment, DMT polymeric film formation were evaluated using different matrix forming polymers or combination thereof, according to the formula given in Table 5 below:

TABLE 5

| Ingredients | Formulation 3 | 4 | 5 | 6 | 7 | 8 |
|---|---|---|---|---|---|---|
| | Film Composition (% w/w) | | | | | |
| DMT | 22.101 | 22.108 | 26.601 | 19.031 | 27.574 | 27.574 |
| Citric Acid | 4.033 | 4.034 | 3.800 | 3.473 | 8.272 | 8.272 |
| L-Cysteine | 0.968 | 0.968 | 0.912 | 0.833 | — | — |
| L-Glutathione | — | — | — | — | 0.248 | 0.248 |
| Sucralose | 0.838 | 0.838 | 0.789 | 0.721 | 0.573 | 0.573 |
| L-Menthol | 1.936 | 1.936 | 1.824 | 1.667 | 1.324 | 1.324 |
| Copovidone (Plasdone S-360) | 23.392 | — | 22.040 | 20.142 | 15.993 | 15.993 |
| Povidone (PVP K-90) | — | 35.058 | — | — | — | — |
| HPC (Nisso HPC-L) | 46.733 | 35.058 | 44.034 | 40.241 | 31.952 | 31.952 |
| HPMC E50 | — | — | 0 | 6.946 | 5.515 | 5.515 |
| Propylene glycol | — | — | — | — | 3.033 | — |
| PEG 300 | — | — | — | — | — | 3.033 |
| Methanol (% w/w solvent composition) | 70 | 70 | 70 | 70 | 70 | 70 |
| Water (% w/w solvent composition) | 30 | 30 | 30 | 30 | 30 | 30 |

The film using the above composition was prepared as follows: DMT and excipients are mixed with methanol-water (70:30) solvent mix to form a homogenous mixture. The resulted mixture was de-aerated. The film was casted using a de-aerated mixture, dried and cut into strips. DMT films were successfully prepared using all the composition as presented in the above table.

Example 3

In various embodiments, DMT observed to be extensively degrade under oxidative stress. Thus, antioxidant(s)/Chelating agent were incorporated in the buccal/sublingual film to stabilize DMT. Films were prepared using different antioxidant using solvent casting method as described in example 2 having the compositions shown in Table 6 below.

TABLE 6

| Ingredient | Formulation 9-19 Formulation Composition (% w/w) |
|---|---|
| DMT | 18.67 |
| PVPK-90 | 27.26 |
| Nisso HPC-L | 54.07 |
| Antioxidant/Chelating Agent | 0-2.0* |
| Methanol (% w/w solvent composition) | 80 |
| Water (% w/w solvent composition) | 20 |

Note:
quantity of antioxidant is compensated with Nisso HPC-L. Formulation without antioxidant was evaluated as a control.
*Refer table below for the antioxidant level used.

Stability of prepared films were evaluated at 40° C./75% RH for 8 weeks utilizing HPLC method to detect impurity levels as shown in Table 7 below.

TABLE 7

| Formulation | Antioxidant/Chelating agent | Antioxidant Content in Film* (% w/w) | T = 0 | 3 W | 6 W | 8 W |
|---|---|---|---|---|---|---|
| | | | (Total Impurity % mg/mg) | | 40° C./75% RH | |
| 9 | EDTA | 0.063 | 1.22 | 0.96 | 2.16 | 2.03 |
| 10 | BHT | 0.059 | 0.77 | 0.92 | 1.65 | 1.45 |
| 11 | Copper chloride dihydrate | 0.0014 | 0.39 | 1.34 | 2.20 | 1.86 |
| 12 | L-Cysteine | 0.83 | 0.38 | 0.65 | 1.05 | 0.76 |
| 13 | Ascorbic acid 6-palmitate | 0.142 | 0.85 | 0.89 | 1.62 | 1.40 |
| 14 | L-glutathione reduced | 0.26 | 0.38 | 0.753 | 1.53 | 1.30 |
| 15 | Propyl gallate | 0.10 | 1.15 | 1.215 | 1.74 | 1.69 |
| 16 | Nutrabiol (pure α-tocopherol) | 0.11 | 0.95 | 1.036 | 1.6 | 1.42 |
| 17 | Tocobiol (mixture of α-, β-, γ- and δ-tocopherols in addition to ascorbyl palmitate) | 0.11 | 0.67 | 0.718 | 1.27 | 1.23 |
| 18 | Ascorbic Acid | 1.72 | 2.10 | 2.254 | 3.43 | 3.16 |
| 19 | Control (Without Antioxidant) | N/A | 0.91 | 1.10 | NA | 1.56 |

From the above stability results, antioxidants were found to improve stability of DMT in polymeric films.

Example 4

Further, stability of DMT was studied at various levels of L-glutathione. Thus, DMT films were prepared using solvent casting method and evaluated for stability utilizing HPLC method as described in Table 8 below.

TABLE 8

| | Formulation | |
|---|---|---|
| | 20 | 21 |
| Ingredients | Film Composition (% w/w) | |
| N,N DMT | 27.816 | 27.65 |
| Citric Acid | 8.206 | 8.24 |
| Antioxidant(s) | — | — |
| L-Glutathione | 0.834 | 1.31 |

TABLE 8-continued

| | Formulation | |
|---|---|---|
| | 20 | 21 |
| Ingredients | Film Composition (% w/w) | |
| L-Menthol | 1.335 | 1.33 |
| Sucralose | 0.578 | 0.57 |
| Copovidone (plasdone s-630) | 16.133 | 16.04 |
| Nisso HPC-L | 32.232 | 32.04 |
| HPMC E50 | 5.563 | 5.53 |
| Maltitol | 5.563 | 5.53 |
| PEG 300 | 1.739 | 1.75 |
| Methanol (% w/w solvent composition) | 70 | 70 |
| Water (% w/w solvent composition) | 30 | 30 |

Stability of prepared films were evaluated at a higher temperature of 50° C. for 1 week utilizing HPLC method as shown in Table 9 below.

TABLE 9

| Formulation | L-Glutathione (% w/w) | Stability conditions | DMT N-oxide | tryptamine | N-m tryptamine | % Imp. (report) | % Imp. (total) | RRT 1.12 API (impurities excluded) % Imp. (report) | % Imp. (total) |
|---|---|---|---|---|---|---|---|---|---|
| 20 | 0.83% | T0 | 0.04 | 0.02 | 0.07 | 0.59 | 0.85 | Not reported | 0.26 |
| | | 1 W/50° C. | 0.13 | 0.04 | 0.15 | 0.86 | 1.02 | 0.28 | 0.44 |
| 21 | 1.3% | T0 | 0.05 | 0.05 | 0.09 | 0.52 | 0.82 | Not reported | 0.30 |
| | | 1 W/50° C. | 0.07 | 0.03 | 0.14 | 0.69 | 1.00 | 0.14 | 0.45 |

L-Glutathione at levels of both 0.83% and 1.3% showed good stability up to 1 week at 50° C. temperature.

Example 5

To evaluate the impact of physical form of DMT on disintegration, dissolution, and permeability across pig buccal mucosa, DMT polymer films were prepared using different solvent composition with and without citric acid according to the formula given in the table 10 below.

TABLE 10

| Ingredients | Formulation | | |
|---|---|---|---|
| | 22 | 23 | 24 |
| | Film Composition (% w/w) | | |
| N,N Dimethyltryptamine | 27.151 | 29.541 | 27.626 |
| Copovidone (Plasdone S-630) | 15.748 | 17.134 | 16.029 |
| Hydroxypropyl Cellulose (Nisso HPC-L) | 31.462 | 34.232 | 32.010 |
| Hydroxypropyl methylcellulose (HPMC E50) | 7.240 | 7.877 | 7.371 |
| Polyethylene glycol 300 | 1.720 | 1.871 | 1.749 |
| L-Glutathione | 1.290 | 1.404 | 1.311 |
| Citric Acid | 8.091 | — | 8.233 |
| Sucralose | 0.564 | 0.614 | 0.571 |
| Maltitol | 5.430 | 5.909 | 5.525 |
| L-Menthol | 1.303 | 1.418 | 1.324 |
| Methanol (% w/w solvent composition) | 50 | — | — |
| Water (% w/w solvent composition) | 50 | 100 | 100 |

The DMT films using the above composition were prepared as follows: DMT and excipients are mixed with either water (100%) or methanol-water (50:50) solvent mix to form a homogenous mixture also called blend. The resulted mixture was de-aerated. The film was casted using a de-aerated mixture, dried and cut into strips. The films were characterized for DMT form using PXRD as presented shown in FIGS. 2 and 3A-3B. FIG. 2 shows the PXRD Spectra of DMT polymer film Formulation 23 (Crystalline Peaks of DMT-Present). FIG. 3A shows the PXRD Spectra of polymer film Formulation 22 (Crystalline Peaks of DMT-Absent). FIG. 3B shows the PXRD Spectra of polymer film Formulation 24 (Crystalline Peaks of DMT-Ab sent).

Based on the PXRD results it was confirmed that DMT is present in amorphous form in formulation 22 and 24. In formulation 22 and 24 DMT was present completely in a solution form in the blend resulting in a film with amorphous DMT. In formulation 24, DMT was completely solubilized in the blend despite excluding of methanol, principally due to the presence of citric acid which helps DMT to completely solubilize in 100% water phase by lowering the blend pH and finally yielded a film with amorphous DMT. Whereas in formulation 23, DMT was present in crystalline form due to exclusion of methanol and citric acid which are necessary to help DMT completely dissolve in the blend.

Based on the above results it is inferred that, DMT should be completely dissolved in the blend to achieve a film formulation with amorphous DMT.

Figure 4A:
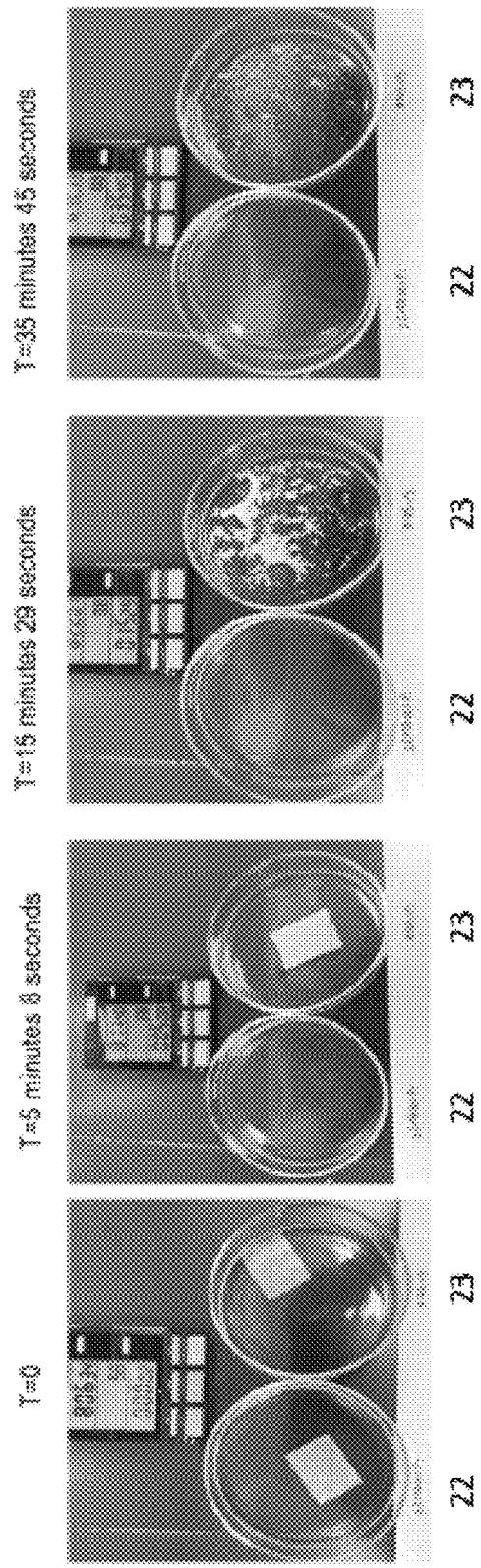
FIG. 4A shows disintegration test for Formulations 22 and 23.
Figure 4B:
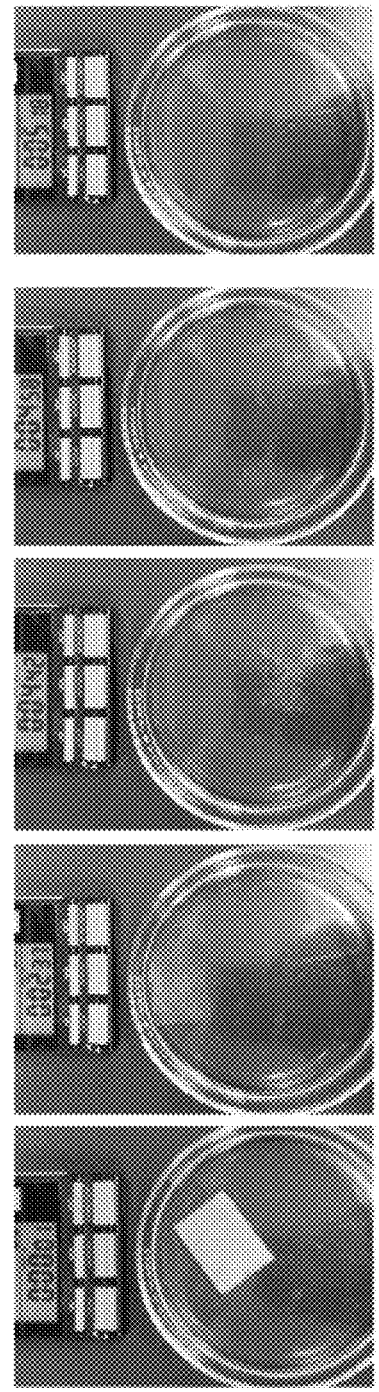
FIG. 4B shows disintegration test for Formulation 24.

Further, prepared films were evaluated for film disintegration and dissolution to understand the impact of DMT physical form in film formulation as shown in FIGS. 4A-4B. Disintegration Time of Formulation 24

Figure 5:
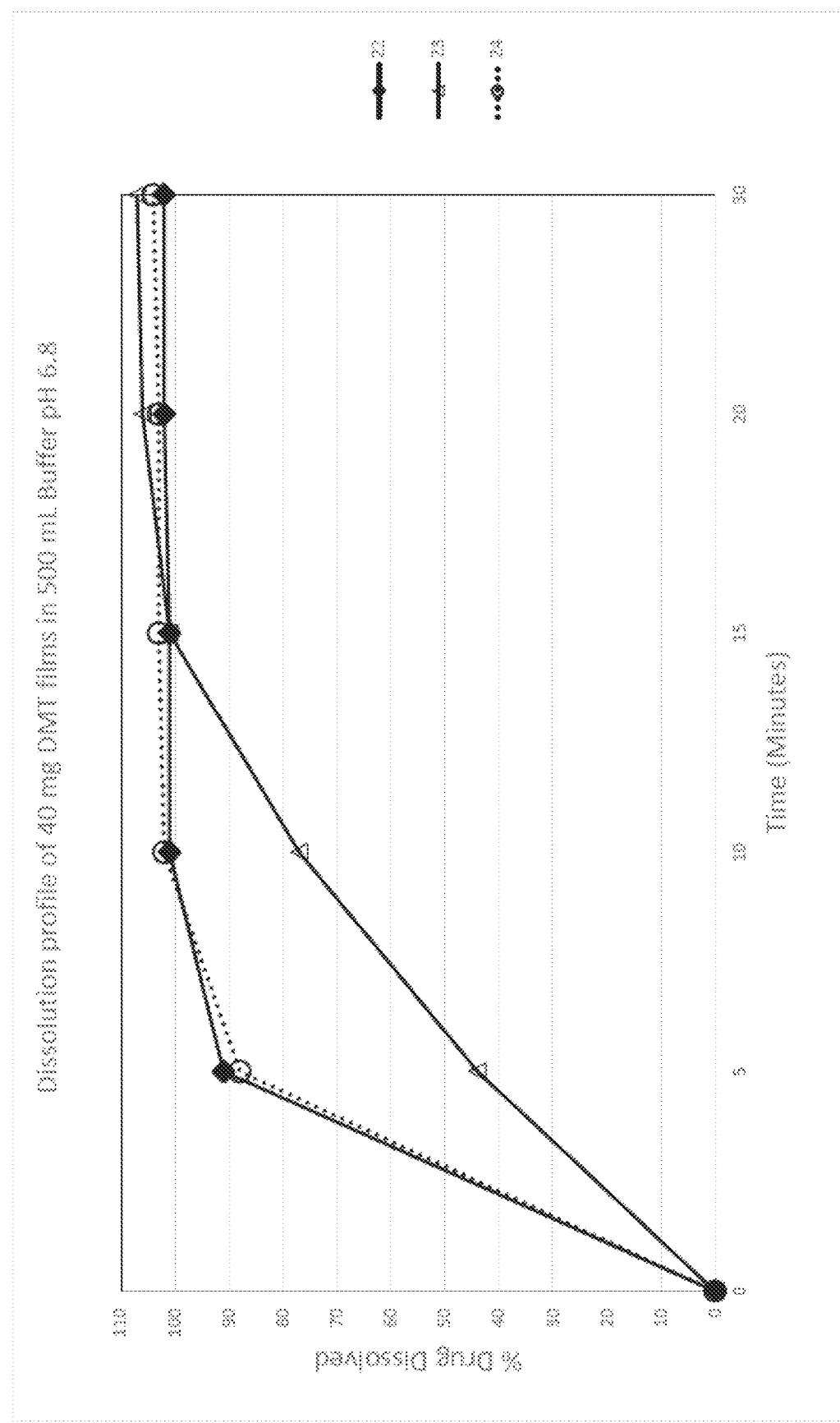
FIG. 5 is a chart showing the dissolution profile for 40 mg DMT films in 500 mL buffer at pH 6 for formulations 22, 23, and 24.

Based on the above presented disintegration results it was confirmed that films with amorphous API (Formulation 22 and 24) rapidly disintegrated within 5 minutes and formed clear solutions in PBS pH 7.0 whereas the film with crystalline API (Formulation 23) showed delayed disintegration at about 15 minutes and film residues were not completely solubilized even after 35 minutes in PBS pH 7.0. Longer disintegration time is not desired for DMT film formulation as it increases chances to swallow undissolved residue which ultimately gets deactivated in GI tract and liver. The disintegration results for Formulations 22-24 are shown in FIG. 5.

Dissolution profile of 40 mg DMT films (Formulation 22, 23 & 24) in 500 mL Buffer pH 6.8

Based on the above presented dissolution results it was confirmed that film with amorphous API (Formulation 22 & 24) showed rapid drug release and more than 80% drug is dissolved within 5 minutes. On the other hand, film with crystalline API (Formulation 23) showed slower dissolution during 5 min. and 10 min. timepoint as compared to amorphous API film. At 15 minutes all three formulations showed complete drug release which is attributed to the complete sink condition in 500 mL of dissolution media volume for film.

Figure 6:
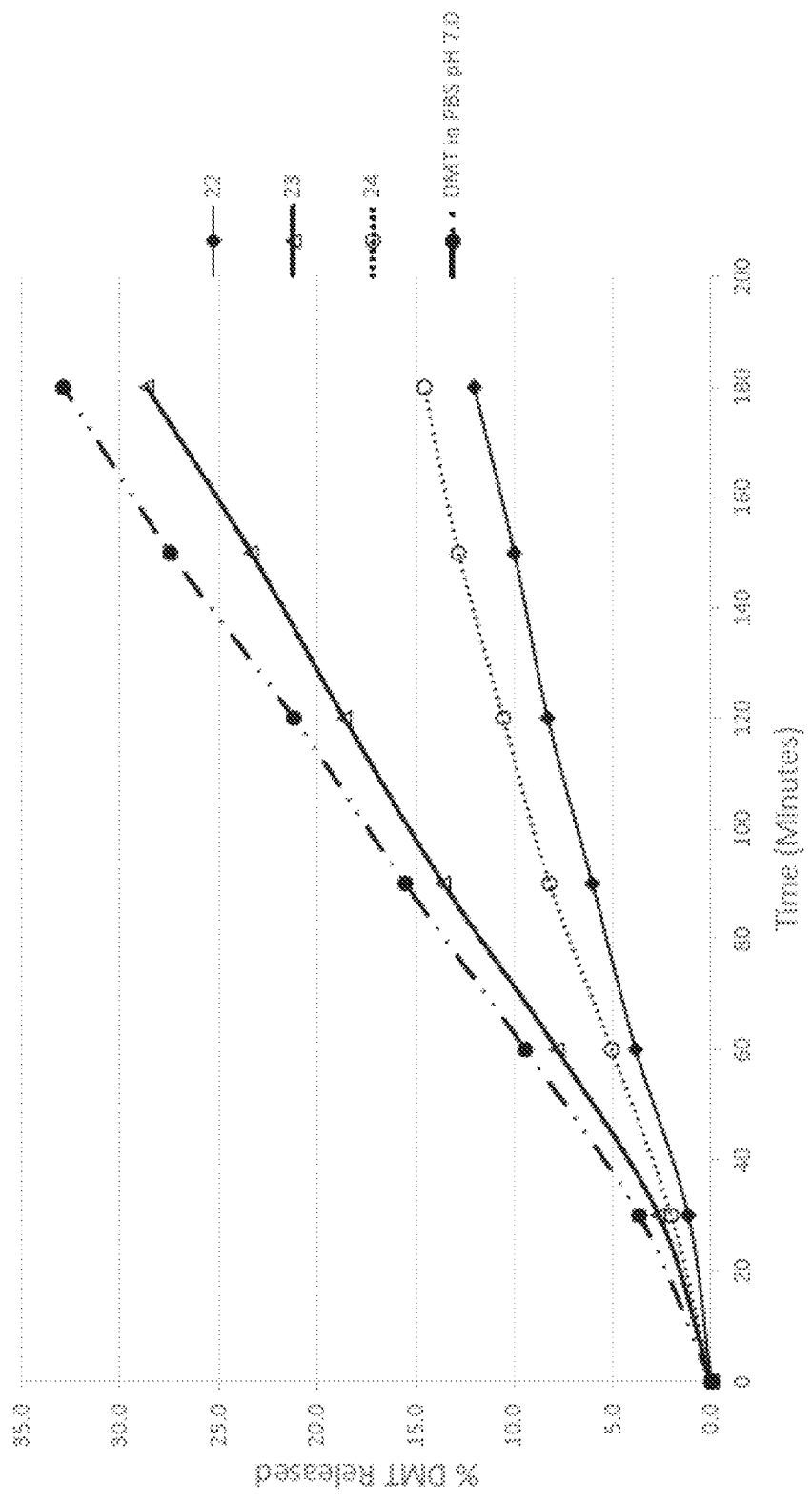
FIG. 6 is a chart showing DMT permeation through porcine mucosa in phosphate buffered solution at pH=7 for formulations 22, 23, and 24, as well as for API (DMT in PBS).

Further, all prepared films are evaluated for the permeability through pig buccal mucosa and compared against the permeability of API dispersion in PBS pH 7.0 as presented in FIG. 6. In one aspect, the present invention involves a DMT polymeric film that releases about 5% or less DMT in 60 minutes, about 15% DMT or less in 180 minutes when measured through pig mucosa in phosphate buffered solution 0.01M pH=7, as shown in FIG. 6. These conditions are seen to be satisfied by formulations 22 and 24 and are not satisfied by formulation 23 or DMT active pharmaceutical ingredient (API) not present in a polymer matrix. The formulation 23 exhibited permeation comparable to the DMT API. For example, at around 180 minutes formulation 23 exhibited approximately 29% while the DMT API exhibited about 33% release as shown in FIG. 6.

Based on the above presented results, DMT exhibited permeability through pig buccal mucosa for films with amorphous DMT (Formulation 22 & 24), crystalline DMT (Formulation 23) and DMT dispersion in PBS pH 7.0.

Further, permeability of DMT film (Formulation 23) and DMT dispersion in PBS pH 7.0 was found to be higher as compared to the Formulation 22 and 24 film which could be attributed to pH of the donor chamber media. Formulation 23 and DMT dispersion in PBS exhibited pH of 8.9 and 9.5 respectively which is close to the pKa of DMT 8.68 and thus it is believed that for formulation 23 and DMT dispersion more unionized DMT could be present in the donor chamber resulting in higher permeability than formulation 22 and 24 films which exhibited pH of 7.6 and 7.8 respectively where more ionized DMT could be present.

Further, to understand the impact of film pH on in-vitro permeability, films with different surface pH were prepared as presented in example 6.

Example 6

In an exemplary embodiment, DMT polymer films were prepared according to the formula given in the table below. The films were prepared with different levels of citric acid to produce pH in the range of pH 5 to 10 and the effect of pH was evaluated for permeability as shown in Table 11.

TABLE 11

| Ingredients | Formulation | | | | |
|---|---|---|---|---|---|
| | 25 (159-32) | 26 (159-29-B) | 27 | 28 (159-66) | 29 (159-73) |
| | Film Composition (% w/w) | | | | |
| DMT | 23.887 | 21.661 | 29.10 | 27.652 | 28.752 |
| Plasdone S-630 | 19.792 | 17.948 | 16.88 | 16.038 | 16.676 |
| Nisso HPC-L | 39.541 | 35.858 | 33.72 | 32.042 | 33.317 |
| HPMC E50 | 6.825 | 6.189 | 5.82 | 5.530 | 5.751 |
| PEG 300 | — | — | 1.76 | 1.751 | 1.754 |
| L-Glutathione | — | — | 1.32 | 1.313 | 0.805 |
| L-cysteine | 0.785 | 0.743 | — | — | — |
| Citric Acid | — | 9.283 | 3.59 | 8.240 | 5.012 |
| Sucralose | 0.709 | 0.643 | 0.60 | 0.574 | 0.597 |
| Maltitol | 6.825 | 6.189 | 5.82 | 5.530 | 5.751 |
| L-Menthol | 1.638 | 1.485 | 1.40 | 1.327 | 1.380 |
| Methanol (% w/w solvent composition) | 70 | 70 | 70 | 70 | 70 |
| Water (% w/w solvent composition) | 30 | 30 | 30 | 30 | 30 |
| Film surface pH | 9.3 | 5.7 | 9.3 | 7.2 | 8.2 |

The DMT films using the above composition were prepared as follows: DMT and excipients are mixed with methanol-water (70:30) solvent mix to form a homogenous mixture. The resulted mixture was de-aerated. The film was casted using a de-aerated mixture, dried and cut into strips. The films were measured for surface pH and data presented in above composition table.

Further, permeability of DMT through prepared films were evaluated using ex-vivo permeation study i.e., porcine buccal mucosa or Permeapad® as presented below.

Figure 7A:
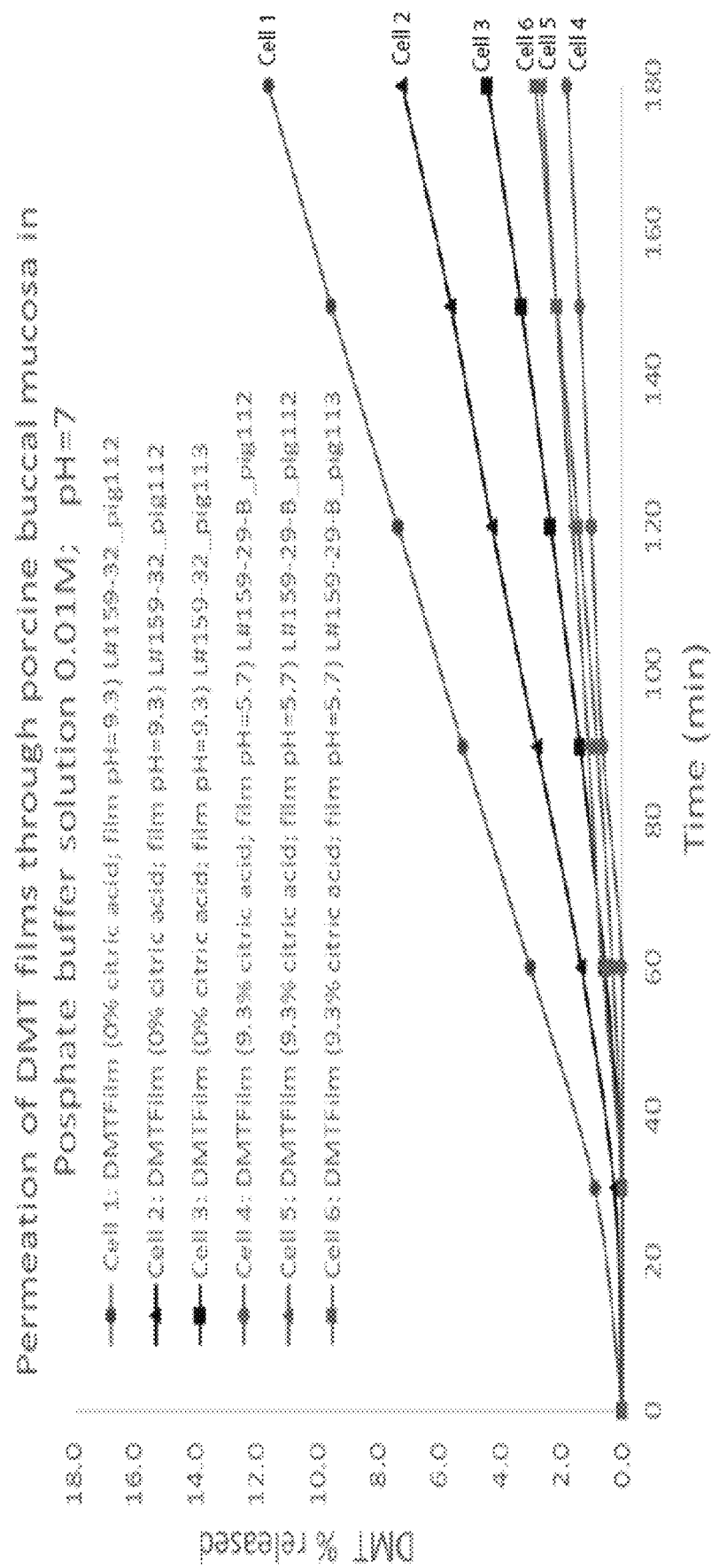
FIG. 7A shows permeation of DMT films through porcine buccal mucosa in phosphate buffered solution 0.1M, pH=7.
Figure 7B:
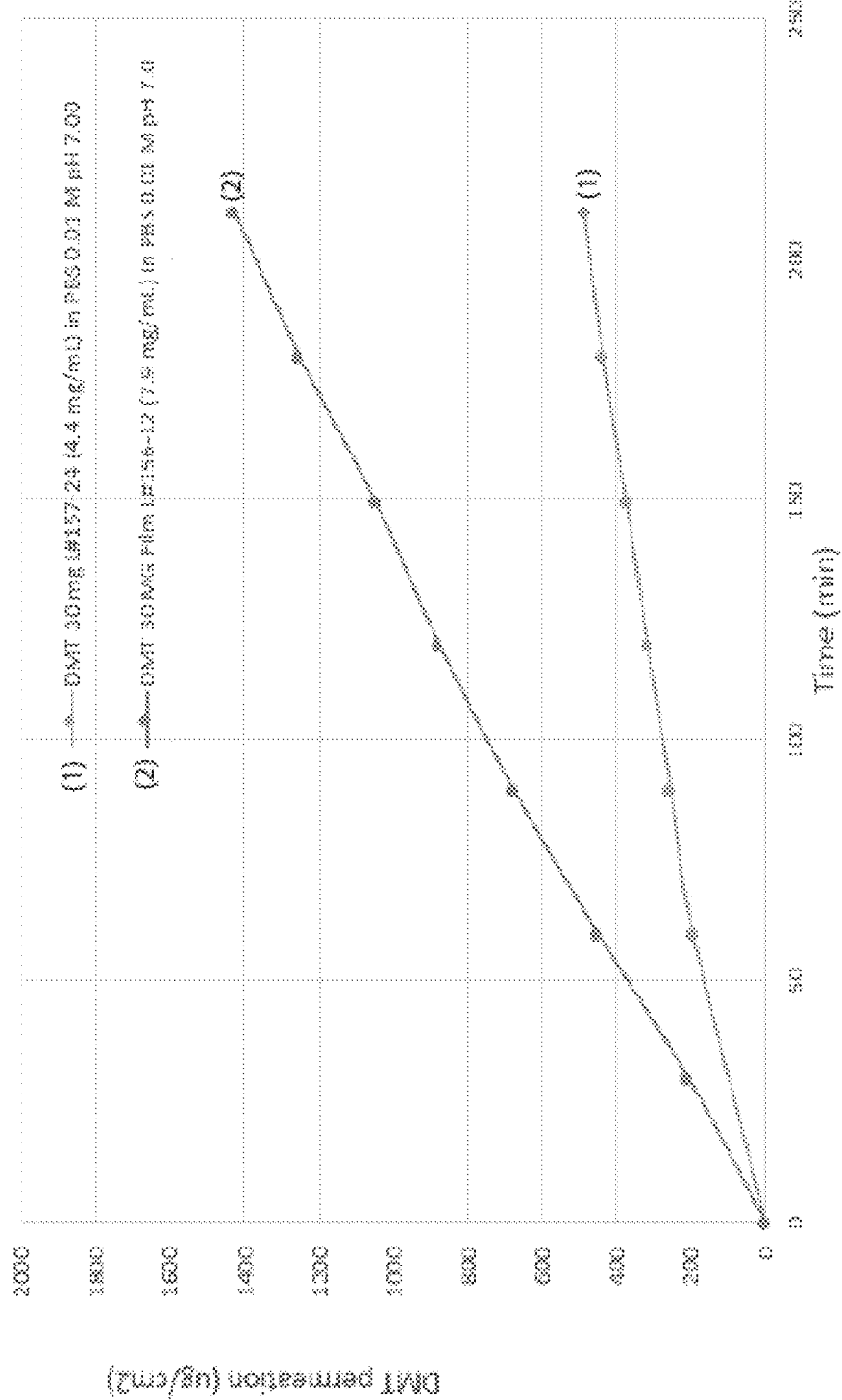
FIG. 7B shows the effect of pH on DMT film permeation through artificial PermeaPad membrane in phosphate buffered solution 0.01M pH=7.

The Permeapad® (Certificate No. 014557268) is the barrier consist of support layer and lipid layer. The barrier is made up of soy phosphatidylcholine S-100 as the lipid layer. In brief, a thin layer of lipid is applied to a hydrophilic support sheet (Putz GmbH, Taunusstein, Germany) in organic solution. The solvent is allowed to evaporate to form the barrier. Permeability of the model drug metoprolol was determined across Permeapad® and compared to literature data for permeation across TR146 cell layers, porcine buccal mucosa ex vivo and in Gottingen minipigs. The results showed a good correlation between Permeapad® and the respective in vitro studies, which indicated that Permeapad® appears useful as a predictive assay for pH dependent permeability for this basic drug substance. Permeapad® is suggested as a preliminary permeability tool for buccal absorption of metoprolol. An excellent 2 IVIVC (R=0.98) was obtained when comparing Papp to the absolute bioavailability of metoprolol administered buccally in the form of a gel to mini-pigs, indicating that in the case of metoprolol Permeapad® can be used to mimic buccal mucosa as a faster and less laborious method as compared to any of the other mentioned methods. See Use of Permeapad® for prediction of buccal absorption: A comparison to in vitro, ex vivo and in vivo method, Hanady Ajine Bibi a, René Holm b,1, Annette Bauer-Brandl a, FIG. 7A shows permeation of DMT films through porcine buccal mucosa in phosphate buffered solution 0.01M, pH=7. FIG. 7B shows the effect of pH on DMT film permeation through artificial PermeaPad membrane in phosphate buffer solution 0.01M, pH=7.

Stability of prepared films were evaluated at 50° C. RH weeks utilizing HPLC method to detect impurity levels as shown in Table 12 below.

TABLE 12

| Formulation | Stability conditions | DMT N-oxide | tryptamine | N-m tryptamine | % Imp. (total) |
|---|---|---|---|---|---|
| 27 (3.59% w/w Citric Acid) | T0 | 0.07 | 0.04 | 0.07 | 0.87 |
| | 1 W/50 C. | 0.23 | 0.03 | 0.14 | 1.23 |
| 28 (8.24% w/w Citric Acid) | T0 | 0.05 | 0.05 | 0.09 | 0.82 |
| | 1 W/50 C. | 0.07 | 0.03 | 0.14 | 1.00 |
| 29 (5% w/w Citric Acid) | T0 | 0.08 | 0.04 | 0.09 | 0.95 |
| | 1 W/50 C. | 0.15 | 0.09 | 0.34 | 1.63 |

The surface pH has showed impact on permeation rate. Films with two extreme levels of citric acid 0% w/w and 9.3% w/w produced surface pH of 9.2 showed better permeation compared to pH 5.7 films respectively. Formulations with citric acid level of 5.0% and 8.2% w/w citric acid produces pH close to saliva pH in oral cavity, as pH 8.2 and 7.5 respectively and both formulations showed satisfactory permeability with artificial membrane as presented in graph. 1 wk stability at 50 C temperature for all formulations showed promising data. Based on the permeability and stability studies, formulation containing citric acid level 4.0-9.0% w/w, more preferably with level 5.0-8.5% w/w is preferred.

Example 7

In an exemplary embodiment, DMT polymer film were prepared according to the formula given in table 13 below.

TABLE 13

| Ingredients | Formulation 30 (RD2021-DEC-01M) Film Composition (% w/w) |
|---|---|
| N,N Dimethyltryptamine | 27.151 |
| Copovidone (Plasdone S-630) | 15.748 |
| Hydroxypropyl Cellulose (Nisso HPC-L) | 31.462 |
| Hydroxypropyl methylcellulose (Hypromellose 2910/Methocel E50) | 7.240 |
| Polyethylene glycol 300 | 1.720 |
| L-Glutathione | 1.290 |
| Anhydrous Citric Acid | 8.091 |
| Sucralose | 0.564 |
| Maltitol | 5.430 |
| L-Menthol | 1.303 |
| Methanol (% w/w solvent composition) | 50 |
| Water (% w/w solvent composition) | 50 |

The buccal/sublingual film using above composition were prepared as follows: DMT and excipients are mixed with methanol-water (50:50) solvent mix to form a homogenous mixture. The resulted mixture was de-aerated. The film was casted using a de-aerated mixture and dried until loss on drying (LOD) of the dried film is achieved, preferably within 2 to 11% w/w to form flexible film sheets. The thickness of the flexible film sheets is preferably within 0.05-0.40 mm. The prepared film sheets comprise amorphous DMT preferably within 3-7 mg/cm$^2$. The individual prepared films were cut into strips of varied sizes and/or weight to achieve any strength, including from 2.5 mg to 80 mg. Preferably from 5 mg to 40 mg. From above batch sheet was cut to form four strengths of 5 mg, 10 mg, 20 mg and 40 mg. Prepared films are characterized for mechanical properties as presented in Table 14 below.

TABLE 14

| Lot # | Folding Endurance | Elongation (%) | Tensile Strength (kPa) |
|---|---|---|---|
| Formulation # 30 (10 mg) | >10 | 62 ± 19 | 245 ± 89 |
| Formulation # 30 (40 mg) | >10 | 61 ± 7 | 158 ± 5 |

Stability of prepared films were evaluated at 2-8 C, 25° C./60% RH, 40° C./75%₀RH for 5 mg and 40 mg strengths utilizing bracketing approach as presented in Tables 15-20 below.

TABLE 15

Stability of DMT Polymer Film (5 mg)

| Batch Number | RD2021-DEC-01P1 |
| Storage Condition | 2-8° C. |
| Container Closure | Each film is packaged in a heat-sealed laminated aluminum pouch. 10 pouches are placed in a box. |

Test Points and Results

| Test | Acceptance Criteria | T0 | 3M | 6M |
|---|---|---|---|---|
| Appearance | Report Result | White to off-white film | White to off-white film | White film |
| Assay (% LC) | 90.0-110.0% | 99.0 | 103.6 | 98.4 |
| Degradation Products (HPLC), % Area | | | | |
| Tryptamine | NMT 1.0% | 0.10 | 0.10 | 0.10 |
| N-Methyl Tryptamine | NMT 1.0% | 0.05 | 0.06 | 0.08 |
| DMT N-Oxide | NMT 1.0% | <0.05 | — | 0.05 |
| Unspecified (RRT XX) | NMT 0.50% | — | — | 0.01 (RRT 0.43) 0.02 (RRT 0.60) 0.01 (RRT 0.97) 0.03 (RRT 1.29) 0.02 (RRT 1.75) |
| Total | NMT 3.0% | 0.15 | 0.16 | 0.23 |
| Water Content (% w/w) | Report Result | 3.5 | 3.9 | — |
| Dissolution | NLT Q (80%) at 15 minutes | >85% in 15 min. | >85% in 15 min. | >85% in 15 min. |

TABLE 16

Stability of DMT Polymer Film (5 mg)

| Batch Number | RD2021-DEC-01P1 |
| Storage Condition | 25° C./60% RH |
| Container Closure | Each film is packaged in a heat-sealed laminated aluminum pouch. 10 pouches are placed in a box. |

Test Points and Results

| Test | Acceptance Criteria | T0 | 2M | 3M | 6M |
|---|---|---|---|---|---|
| Appearance | Report Result | White to off-white film | Yellow film | Yellow film | Yellow film |
| Assay (% LC) | 90.0-110.0% | 99.0 | 103.0 | 102.2 | 99.4 |
| Degradation Products (HPLC), % Area | | | | | |
| Tryptamine | NMT 1.0% | 0.10 | 0.10 | 0.09 | 0.08 |
| N-Methyl Tryptamine | NMT 1.0% | 0.05 | 0.10 | 0.10 | 0.15 |
| DMT N-Oxide | NMT 1.0% | <0.05 | 0.05 | 0.06 | 0.15 |
| Unspecified (RRT XX) | NMT 0.50% | — | — | — | 0.02 (RRT 0.43) 0.03 (RRT 0.60) 0.03 (RRT 0.97) 0.03 |

TABLE 16-continued

Stability of DMT Polymer Film (5 mg)

|  |  |  |  |  | (RRT 1.19) 0.03<br>(RRT 1.29) 0.01<br>(RRT 1.75) |
|---|---|---|---|---|---|
| Total | NMT 3.0% | 0.15 | 0.25 | 0.25 | 0.38 |
| Water Content (% w/w) | Report Result | 3.5 | — | 4.6 | — |
| Dissolution | NLT Q (80%) at 15 minutes | >85% in 15 min. | >85% in 15 min. | >85% in 15 min. | >85% in 15 min. |

TABLE 17

Stability of Polymer Film (5 mg)

| Batch Number | RD2021-DEC-01P1 |
|---|---|
| Storage Condition | 40° C./75% RH |
| Container Closure | Each film is packaged in a heat-sealed laminated aluminum pouch. 10 pouches are placed in a box. |

Test Points and Results

| Test | Acceptance criteria | T0 | 1 M | 2 M | 3 M | 6 M |
|---|---|---|---|---|---|---|
| Appearance | Report Result | White to off-white film | — | Yellow film | Yellow film | Yellow film |
| Assay (% LC) | 90.0-110.0% | 99.0 | 103.0 | 104.5 | 99.8 | 103.6 |
| Degradation Products (HPLC), % Area |  |  |  |  |  |  |
| Tryptamine | NMT 1.0% | 0.10 | 0.10 | 0.08 | 0.07 | 0.04 |
| N-Methyl Tryptamine | NMT 1.0% | 0.05 | 0.10 | 0.14 | 0.16 | 0.22 |
| DMT N-Oxide | NMT 1.0% | <0.05 | 0.06 | 0.19 | 0.26 | 0.53 |
| Unspecified (RRT XX) | NMT 0.50% | — | — | — | 0.07 (RRT 1.18) | 0.02 (RRT 0.43)<br>0.02 (RRT 0.60)<br>0.07 (RRT 0.97)<br>0.18 (RRT 1.19)<br>0.03 (RRT 1.29)<br>0.07 (RRT 1.75) |
| Total | NMT 3.0% | 0.15 | 0.26 | 0.41 | 0.56 | 1.07 |
| Water Content (% w/w) | Report Result | 3.5 | — | — | 4.3 | — |
| Dissolution | NLT Q (80%) at 15 minutes | >85% in 15 min. | — | >85% in 15 min | >85% in 15 min | >85% in 15 min. |

TABLE 18

Stability of DMT Polymer Film (40 mg)

| Batch Number | RD2021-DEC-01P4 |
|---|---|
| Storage Condition | 2-8° C. |
| Container Closure | Each film is packaged in a heat-sealed laminated aluminum pouch. 10 pouches are placed in a box. |

Test Points and Results

| Test | Acceptance criteria | T0 | 3M | 6M |
|---|---|---|---|---|
| Appearance | Report Result | White to off-white film | White to off-white film | White film |

TABLE 18-continued

Stability of DMT Polymer Film (40 mg)

| | | | | |
|---|---|---|---|---|
| Assay (% LC) | 90.0-110.0% | 99.7 | 100.7 | 96.2 |
| Degradation Products (HPLC), % Area | | | | |
| Tryptamine | NMT 1.0% | 0.10 | 0.10 | 0.09 |
| N-Methyl Tryptamine | NMT 1.0% | 0.05 | 0.06 | 0.08 |
| DMT N-Oxide | NMT 1.0% | — | — | 0.06 |
| Unspecified (RRT XX) | NMT 0.50% | — | — | 0.01 (RRT 0.43) 0.02 (RRT 0.60) 0.01 (RRT 0.97) 0.01 (RRT 1.29) 0.07 (RRT 1.75) |
| Total | NMT 3.0% | 0.15 | 0.15 | 0.23 |
| Water Content (% w/w) | Report Result | 3.5 | 3.6 | — |
| Dissolution | NLT Q (80%) at 15 minutes | >85% in 15 min. | >85% in 15 min. | >85% in 15 min. |

TABLE 19

Stability of DMT Polymer Film (40 mg)

Batch Number: RD2021-DEC-01P4
Storage Condition: 25° C./60% RH
Container Closure: Each film is packaged in a heat-sealed laminated aluminum pouch. 10 pouches are placed in a box.

Test Points and Results

| Test | Acceptance criteria | T0 | 2M | 3M | 6M |
|---|---|---|---|---|---|
| Appearance | Report Result | White to off-white film | Yellow film | Yellow film | Yellow film |
| Assay (% LC) | 90.0-110.0% | 99.7 | 99.3 | 99.4 | 96.6 |
| Degradation Products (HPLC), % Area | | | | | |
| Tryptamine | NMT 1.0% | 0.10 | 0.10 | 0.10 | 0.09 |
| N-Methyl Tryptamine | NMT 1.0% | 0.05 | 0.09 | 0.11 | 0.14 |
| DMT N-Oxide | NMT 1.0% | — | — | 0.07 | 0.08 |
| Unspecified (RRT XX) | NMT 0.50% | — | 0.05 | — | 0.01 (RRT 0.43) 0.02 (RRT 0.60) 0.02 (RRT 0.97) 0.03 (RRT 1.19) 0.03 (RRT 1.29) 0.01 (RRT 1.75) |
| Total | NMT 3.0% | 0.15 | 0.24 | 0.28 | 0.31 |
| Water Content (% w/w) | Report Result | 3.5 | — | 4.0 | — |
| Dissolution | NLT Q (80%) at 15 minutes | >85% in 15 min. | >85% in 15 min. | >85% in 15 min. | >85% in 15 min. |

TABLE 20

| Stability of DMT Polymer Film (40 mg) | | | | | | |
|---|---|---|---|---|---|---|
| Batch Number | RD2021-DEC-01P4 | | | | | |
| Storage condition | 40° C./75% RH | | | | | |
| Container Closure | Each film is packaged in a heat-sealed laminated aluminum pouch. 10 pouches are placed in a box. | | | | | |

| | | Test Points and Results | | | | |
|---|---|---|---|---|---|---|
| Test | Acceptance criteria | T0 | 1 M | 2 M | 3 M | 6 M |
| Appearance | Report Result | White to off-white film | — | Yellow film | Yellow film | Yellow film |
| Assay (% LC) | 90.0-110.0% | 99.7 | 98.0 | 101.1 | 98.9 | 98.9 |
| Degradation Products (HPLC), % Area | | | | | | |
| Tryptamine | NMT 1.0% | 0.10 | 0.10 | 0.08 | 0.07 | 0.04 |
| N-Methyl Tryptamine | NMT 1.0% | 0.05 | 0.09 | 0.13 | 0.15 | 0.22 |
| DMT N-Oxide | NMT 1.0% | — | — | 0.08 | 0.11 | 0.25 |
| Unspecified (RRT XX) | NMT 0.50% | — | — | — | 0.05 (RRT 1.18) | 0.02 (RRT 0.43) 0.04 (RRT 0.97) 0.14 (RRT 1.19) 0.03 (RRT 1.29) 0.07 (RRT 1.75) |
| Total | NMT 3.0% | 0.15 | 0.19 | 0.29 | 0.38 | 0.68 |
| Water Content (% w/w) | Report Result | 3.5 | — | — | 4.3 | — |
| Dissolution | NLT Q (80%) at 15 minutes | >85% in 15 min. | — | >85% in 15 min. | >85% in 15 min. | >85% in 15 min. |

Figure 8:
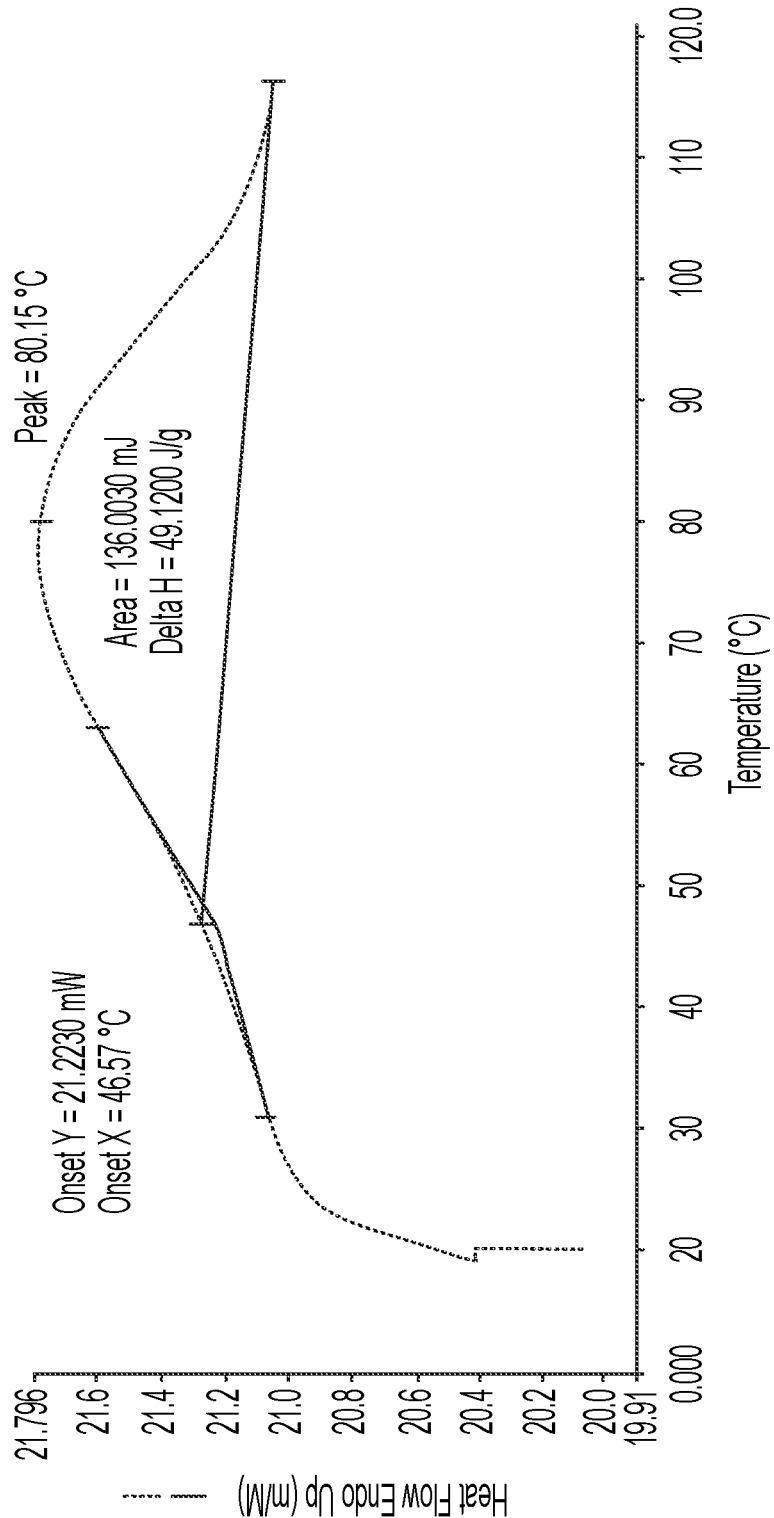
FIG. 8 shows DSC Spectra of DMT polymeric film (Lot #RD-2021Dec-01P4)
Figure 9:
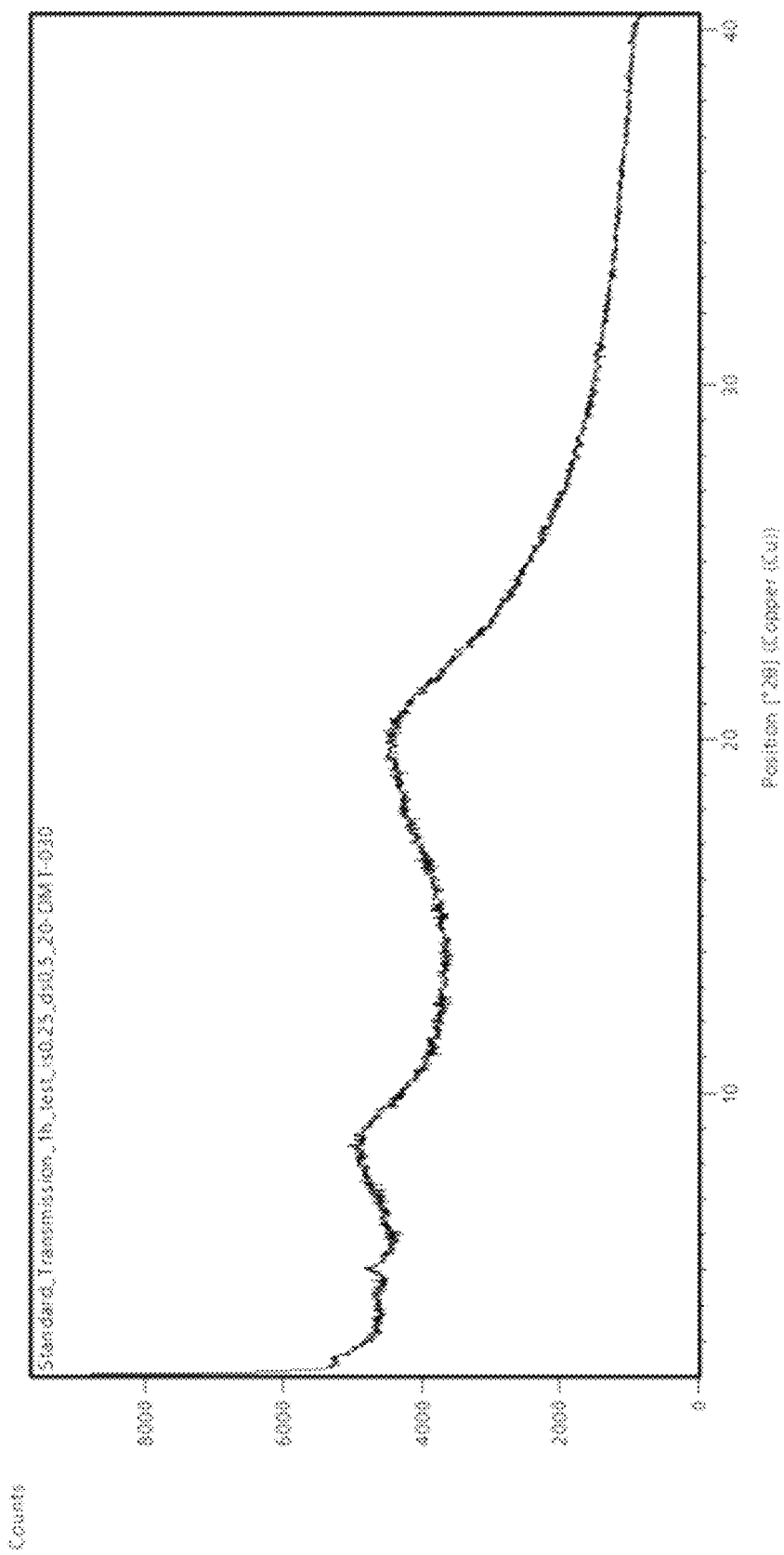
FIG. 9 shows PXRD Spectra of DMT polymeric film (Lot #RD-2021Dec-01P4)

Further during the manufacturing of buccal film, crystalline form of DMT (Form I or IV) was used to manufacture a polymeric film and the manufacturing process produced amorphous form of DMT in the film formulation. Conversion of the amorphous form was confirmed using PXRD and DSC spectra as presented below. Specifically, it is noted that the PXRD diffractogram is free of crystalline peaks. Whereas the DSC spectrum lacks sharp melting endotherm of crystalline DMT and/or indication of phase change (e.g., glass transition temperature). Conversion of DMT to amorphous form is critical for the buccal film formulation to achieve high aqueous solubility to ensure drug solubilization at the mucosal surface in buccal cavity to facilitate transmucosal permeation of DMT and systemic absorption as shown in FIG. 8. The PXRD Spectra of DMT Polymer Film (Lot #RD-2021DEC-01P4) is shown in FIG. 9, confirming the absence of crystalline peaks, including any peaks associated with DMT.

Figure 10A:
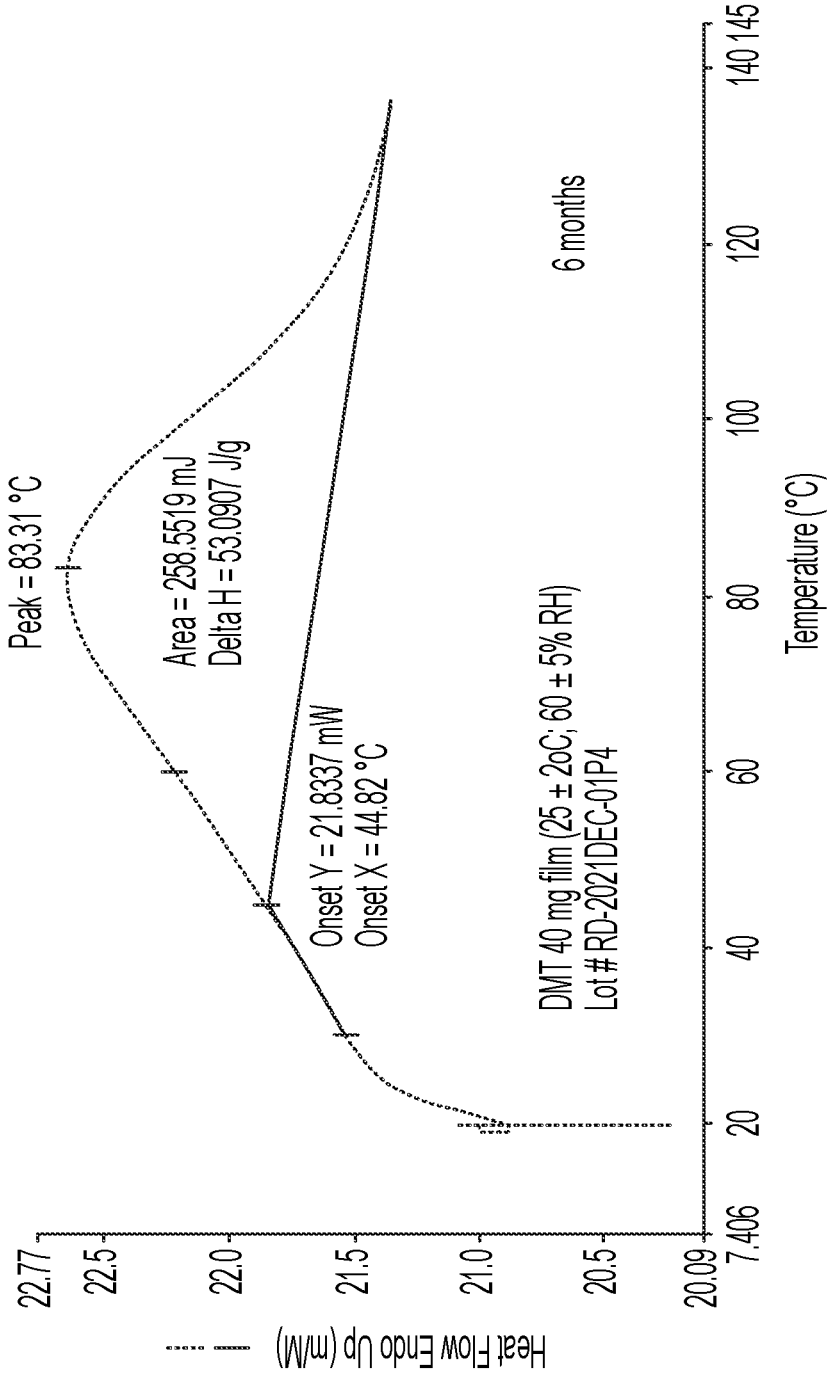
FIG. 10A shows DSC Spectra of DMT polymeric film (Lot #RD-2021Dec-01P4) 6 Month 25 C/60% relative humidity.
Figure 10B:
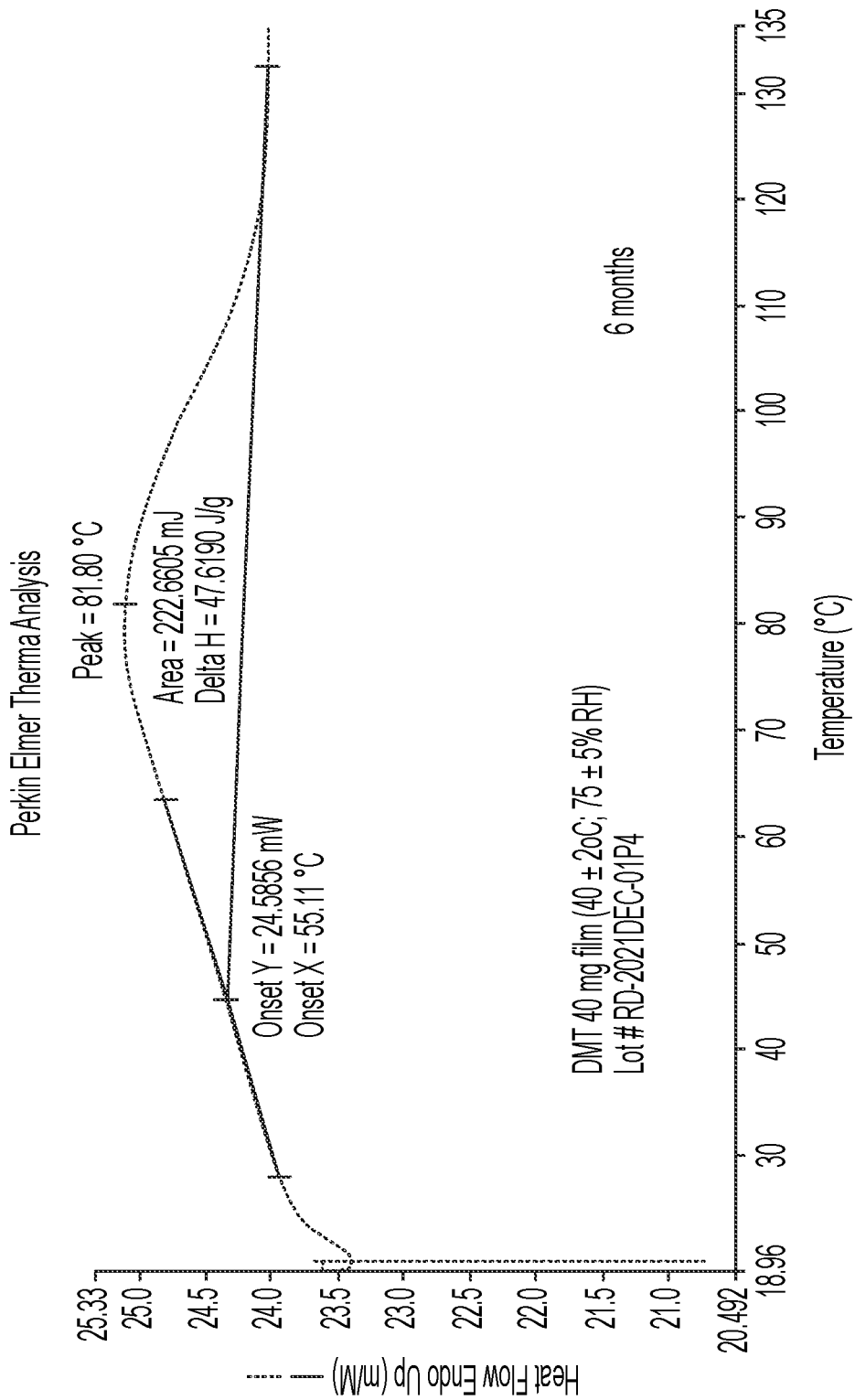
FIG. 10B shows DSC Spectra of DMT polymeric film (Lot #RD-2021Dec-01P4) 6 Month 40 C/75% relative humidity.

In the present invention amorphous form of DMT has been generated successfully using combination of various polymers. Further, addition of these polymers helps keep stable amorphous form in the film even under accelerated storage condition i.e., room temperature (25° C./60% RH) and even at worst conditions of 40° C./75% RH up to 6M as shown in FIGS. 10A-10B. FIG. 10A shows DSC Spectra of Polymer Film (Lot #RD-2021Dec-01P4) 6 Month 40° C./75% relative humidity. FIG. 10B shows DSC Spectra of DMT Polymer Film (Lot #RD-2021Dec-01P4) 6 Month 40° C./75% relative humidity.

Figure 11A:
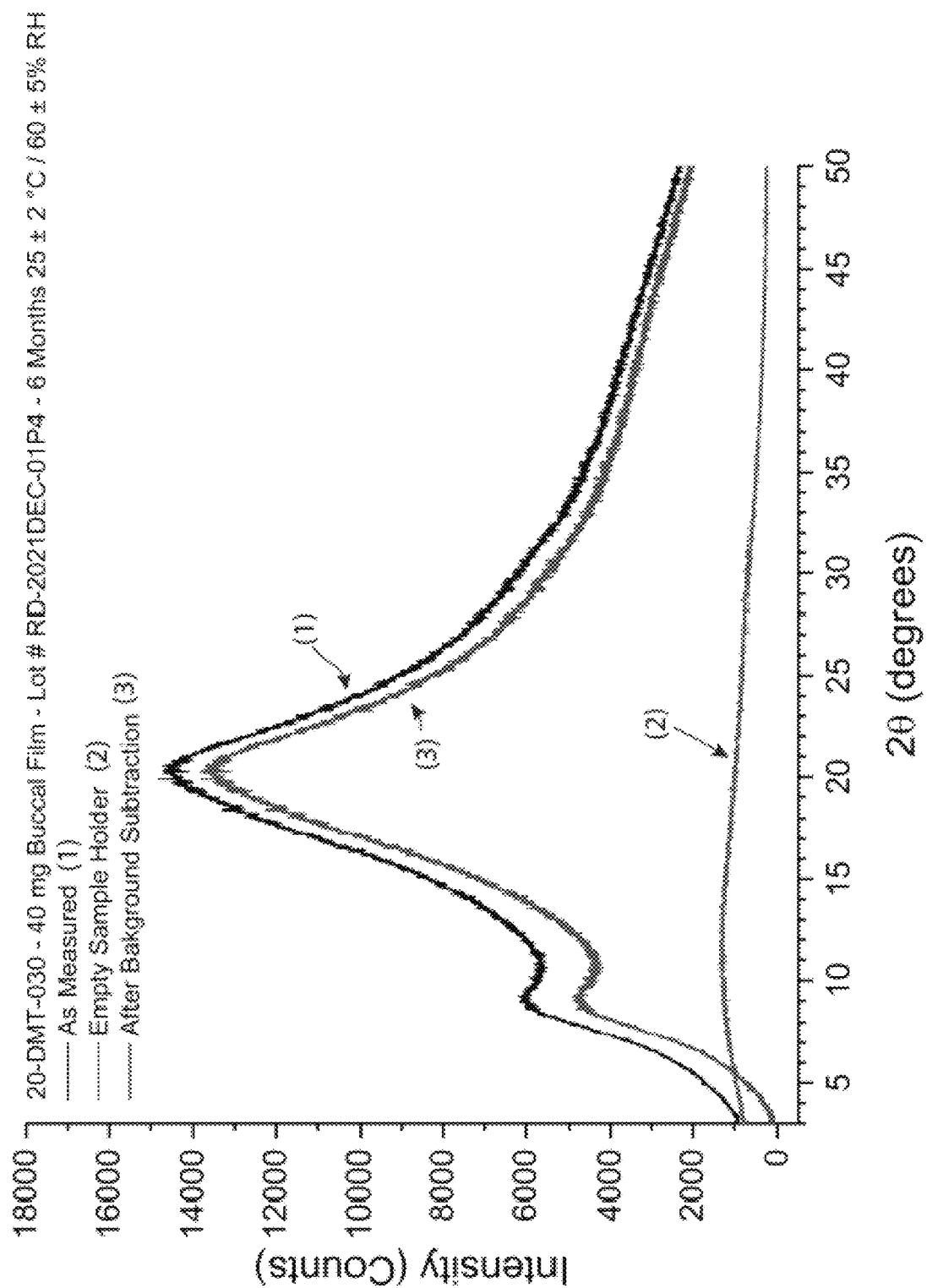
FIG. 11A shows PXRD Spectra of DMT polymeric film (Lot #RD-2021Dec-01P4) 6 Month 25 C/60% relative humidity showing the absence of crystalline peaks, including any peaks indicative of DMT.
Figure 11B:
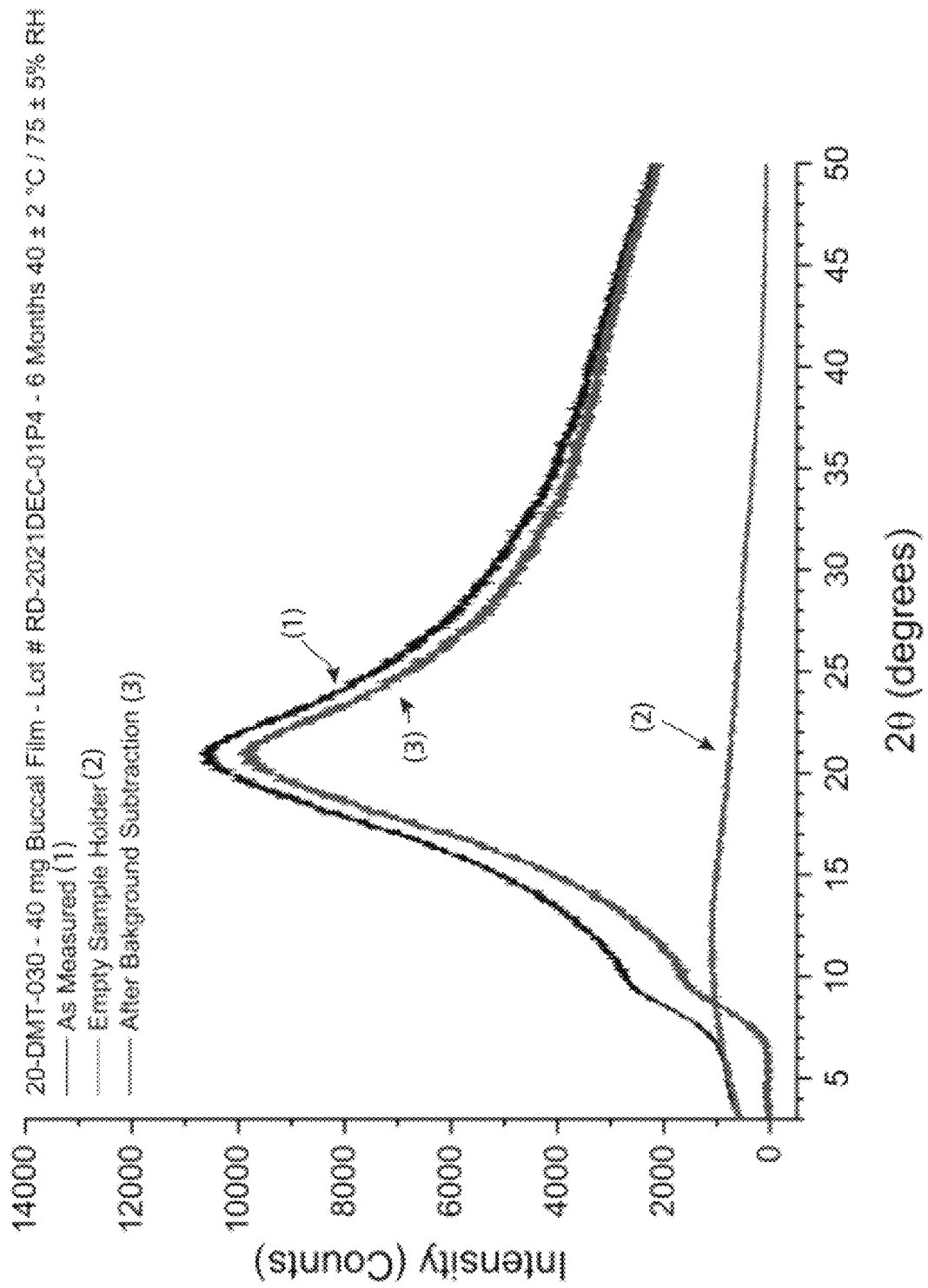
FIG. 11B shows PXRD Spectra of DMT polymeric film (Lot #RD-2021Dec-01P4) 6 Month 40 C/75% relative humidity showing the absence of crystalline peaks, including any peaks indicative of DMT.

FIG. 11A shows the shows PXRD Spectra of DMT Polymer Film (Lot #RD-2021Dec-01P4) 6 Month 25° C./60% relative humidity showing the absence of crystalline peaks, including any peaks indicative of DMT. FIG. 11B shows PXRD Spectra of DMT Polymer Film (Lot #RD-2021Dec-01P4) 6 Month 40° C./75% relative humidity showing the absence of crystalline peaks, including any peaks indicative of DMT.

The buccal film was tested for disintegration with 20 mL Phosphate Buffer Saline pH 7.0 in Petri dish. The film disintegration time was found to be between 3-10 minutes.

Also, the solubility of buccal film and neat API (crystalline DMT) was measured in Phosphate buffer saline pH 6.8 and found to be 24.6 mg/mL and 2.3 mg/mL respectively. This improved solubility also suggests there was a several fold increase in solubility of DMT in polymeric films compared to its crystalline form.

Figure 12:
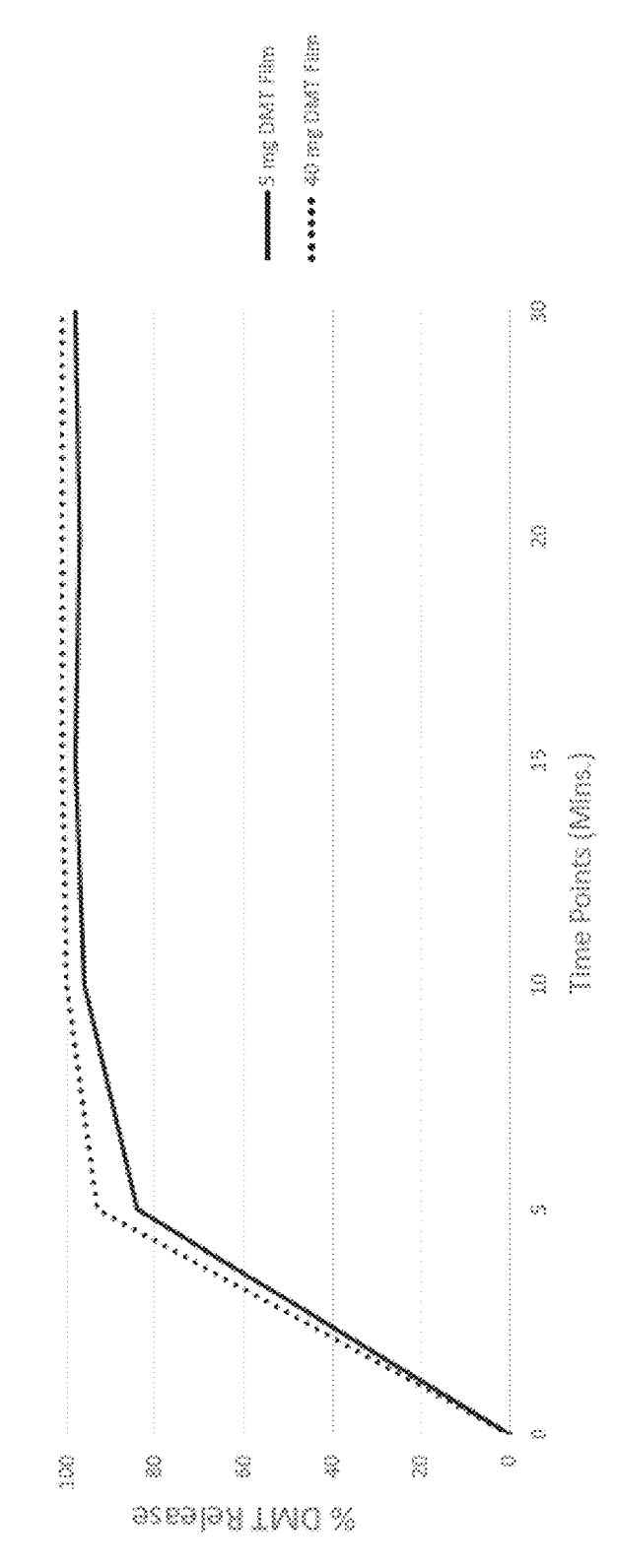
FIG. 12 shows dissolution profiles for 5 mg and 40 mg DMT films in 500 mL Buffer pH=6.8.

Further, dissolution of 5 mg and 40 mg Polymer Film was carried out in 500 mL phosphate buffer pH 6.8 using USP type 2 dissolution apparatus at 50 rpm. Dissolution data are presented in the below graph. Film showed rapid dissolution with complete drug release within 15 minutes. Stability of these films are evaluated at 2-8° C., 25° C./60% RH and 40° C./75% RH for 6 months and all films showed rapid dissolution with more than 85% drug release in 15 minutes further confirming amorphous form retention in film formulation. FIG. 12 shows dissolution profiles for 5 mg and 40 mg DMT films in 500 mL Buffer pH=6.8.

Figure 13A:
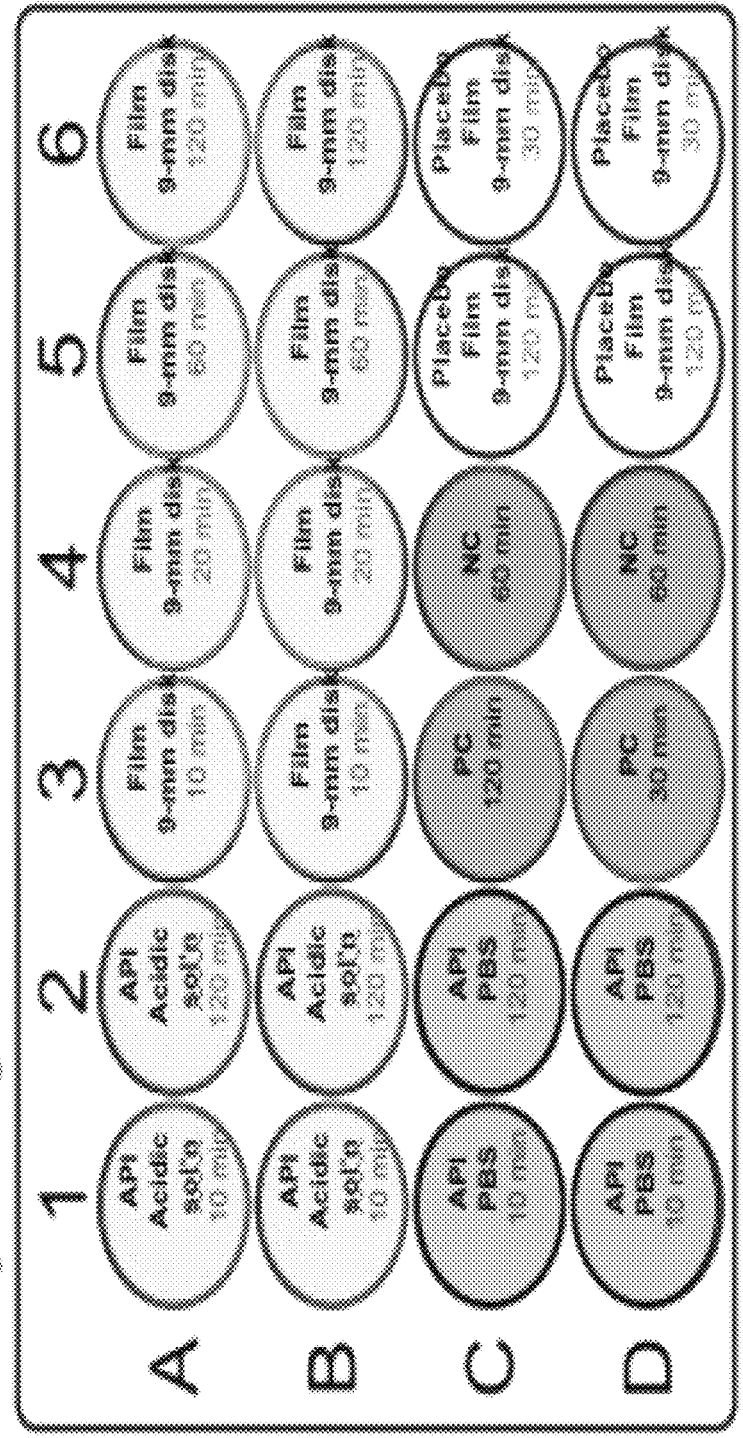
FIG. 13A shows the study design for in-vitro tolerability of prepared buccal film evaluated using the EpiOral in vitro tissue model and evaluating cell viability using MTT assay.
Figure 13B:
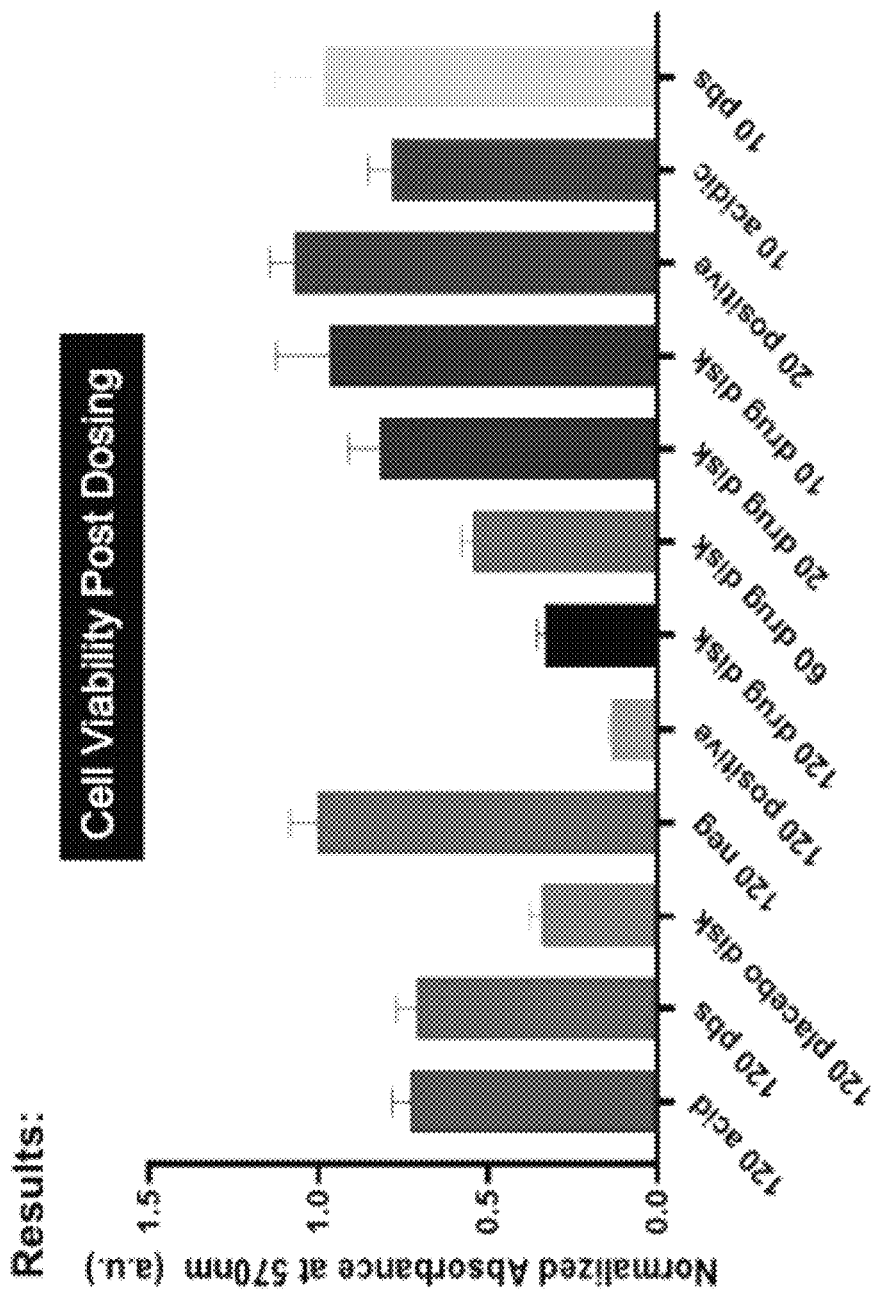
FIG. 13B shows the results of cell viability testing after dosing according to the study design shown in FIG. 13A.

Further, in-vitro tolerability of prepared buccal film was evaluated using the EpiOral in vitro tissue model and evaluating cell viability using MTT assay. The study design and cell viability results are shown in FIGS. 13A and 13B, respectively.

The study was performed using positive control with 1.0% Triton X100 and a negative control without dosing the formulation. The samples included neat API in acidic and basic solutions along with placebo and formulated DMT films at different time points as shown in above study design.

The results based on cell viability were presented as bar graph in above figure showed promising values at 10, 20 and up to 60 minutes when comparing with negative control and positive control. The film showed faster disintegration time less than 10 minutes and about 90% dissolution in 5 minutes. DMT polymer film was found to demonstrate more than 80% cell viability at 20 minutes time point and based on disintegration and dissolution data, it is expected that film will dissolve in buccal mucosa within 20 minutes. Hence, DMT polymer film is unlikely to cause buccal mucosal irritation during the clinical studies.

Based on the physicochemical characterization, in-vitro tolerability and ex-vivo permeability data it is expected that the amorphous form of DMT from the film formulation will be sufficiently solubilized/rapidly dissolved at the buccal site. Further, based on the favorable surface pH, solubilized form of DMT should exhibit rapid transmucosal permeability (rapid onset) and in-vivo bioavailability.

Example 8

Alternatively, or in addition, amorphous DMT can also be manufactured using spray drying process. Briefly, polymer and/or stabilizer and DMT are mixed in a suitable solvent/s mixture to form a solution followed by spray drying at controlled conditions to form stable amorphous DMT powder. The composition of this polymer is shown in Table 21 below.

TABLE 21

| Ingredients | Formulation 31 Composition (% w/w) |
|---|---|
| N,N Dimethyltryptamine | 20.0-90.0 |
| Polymer (e.g., hydroxypropyl cellulose, Copovidone, hydroxypropyl methylcellulose) | 5.0-80.0 |
| Buffering Agent (e.g., citric acid, tartric acid, succinic acid) | 0.0-10.0 |
| Stabilizer (e.g., casein) | 0.0-50.0 |
| Orgnaic Solvent (e.g., Methanol, Ethanol, Methylethyl Ketone) (% w/w solvent composition) | 0-100 |
| Water (% w/w solvent composition) | 0-100 |

Further, amorphous DMT can be formulated as tablets using direct compression process. Briefly, spray dried N,N Dimethyltryptamine powder is blended with filler/diluent, binder, disintegrant, glidant and lubricant to produce a powder blend which is subsequently compressed to form a tablet. The composition of such tablet is shown in Table 21 below.

TABLE 21

| Ingredients | Formulation 31-A Composition (% w/w) |
|---|---|
| Spray dried N,N Dimethyltryptamine Powder | 10.0-80.0 |
| Filler/Diluent (e.g., Microcrystalline cellulose, Lactose, Starch) | 20.0-90.0 |
| Binder (e.g., Hypromellose, Polyvinyl pyrrolidone, Starch) | 0.0-25.0 |
| Disintegrant (e.g., Cellulose, Polyvinyl pyrrolidone, Starch) | 0.5-10.0% |
| Glidant | 0.0-5.0% |
| Lubricant | 0.0-5.0% |

Furthermore, amorphous DMT can also be formulated as polymeric film, tablets such as fast or rapid disintegrating tablets, rapidly dissolving tablets, orodispersible tablets, bi-layer or multi-layer tablets, mucoadhesive tablets, etc. or any other suitable dosage form.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A mucoadhesive therapeutic composition comprising:
a pharmaceutically effective amount of an active DMT agent, the active DMT agent comprising N, N-dimethyltryptamine or a pharmaceutically acceptable salt thereof, wherein the pharmaceutically effective amount of the active DMT agent is about 0.5% to about 60% by weight of the mucoadhesive therapeutic composition; and
a polymeric carrier matrix,- the polymeric carrier matrix stabilizing the DMT agent in an amorphous form within the mucoadhesive therapeutic composition, wherein the polymeric carrier matrix is present in the mucoadhesive therapeutic composition in an amount of 15 to 80 percent by weight of the mucoadhesive therapeutic composition, the polymeric carrier matrix comprising at least one cellulose derivative and a copolymer of N-vinyl-2-pyrrolidone and vinyl acetate, the cellulose derivative being selected from hydroxyethyl cellulose, hydroxypropyl cellulose, hydroxypropyl methylcellulose, or combinations thereof,
wherein the stabilization of the DMT agent in an amorphous form is characterized by a powder x-ray diffractogram free of any discernable peaks that are attributable to the active DMT agent.

2. The mucoadhesive therapeutic composition of claim 1, wherein the mucoadhesive therapeutic composition is suitable for buccal or sublingual administration.

3. The mucoadhesive therapeutic composition of claim 1, wherein the mucoadhesive therapeutic composition is characterized by a differential scanning calorimetry (DSC) spectrum lacking a sharp melting endotherm of crystalline DMT and/or lacking an indication of phase change.

4. The mucoadhesive therapeutic composition of claim 1, wherein the pharmaceutical composition is capable of producing a $T_{max}$ between 10 min to 90 min upon administration.

5. The mucoadhesive therapeutic composition of claim 1, wherein the polymeric carrier matrix further comprises polyacrylic acid, polyacrylate, polyethylene oxide, polyvinyl alcohol, propylene glycol alginate ester, tragacanth, alginate, a gum, a soluble starch, gelatin, lectin, pectin, or chitosan, or a mixture thereof.

6. The mucoadhesive therapeutic composition of claim 1, wherein the mucoadhesive therapeutic composition comprises
about 0.1% to about 30% by weight of a permeation enhancer.

7. The mucoadhesive therapeutic composition of claim 1, wherein the pharmaceutically effective amount of the active DMT agent is about 0.5% to about 60% by weight of the mucoadhesive therapeutic composition.

8. The mucoadhesive therapeutic composition of claim 1, wherein the polymeric carrier matrix is present in the mucoadhesive therapeutic composition in an amount of 50 to 60 percent by weight of the mucoadhesive therapeutic composition.

9. The mucoadhesive therapeutic composition of claim 1, further comprising 0.5% to 20% by weight of a plasticizer.

10. The mucoadhesive therapeutic composition of claim 1, further comprising 0.1% to 10% by weight of a buffering agent.

11. The mucoadhesive therapeutic composition of claim 1, further comprising 0.1% to 5% by weight of an antioxidant.

12. The mucoadhesive therapeutic composition of claim 6, wherein the polymeric carrier matrix comprises hydroxypropyl cellulose, a copolymer of N-vinyl-2-pyrrolidone and vinyl acetate, and hydroxypropyl methylcellulose.

13. The mucoadhesive therapeutic composition of claim 1, wherein DMT or a pharmaceutically acceptable salt thereof is capable of being substantially fully solubilized and released in greater than 1 minute and less than 40 minutes following administration of the composition to a patient in need thereof.

14. An oral transmucosal film comprising the mucoadhesive therapeutic composition of claim 1.

15. The oral transmucosal film claim 14, wherein the oral transmucosal film has a thickness that is 0.01 mm to 1.5 mm.

16. A method of treatment of a disease or disorder, the disease or disorder being an anxiety disorder or mood disorder, wherein the method comprises administering a therapeutically effective amount of the composition of claim 1 to a patient in need thereof.

17. The method of claim 16, wherein the administration is sublingual or buccal.

18. The mucoadhesive therapeutic composition of claim 1, wherein the composition further comprises a buffering agent and an antioxidant.

19. The method of claim 16, wherein the disease or disorder is treatment-resistant depression.

20. A mucoadhesive bilayer film product comprising
the oral transmucosal film of claim 14; and
an inactive backing layer.

* * * * *

UNITED STATES PATENT AND TRADEMARK OFFICE
CERTIFICATE OF CORRECTION

| | | |
|---|---|---|
| PATENT NO. | : 12,128,027 B2 | Page 1 of 1 |
| APPLICATION NO. | : 18/120033 | |
| DATED | : October 29, 2024 | |
| INVENTOR(S) | : Srinivas G. Rao et al. | |

It is certified that error appears in the above-identified patent and that said Letters Patent is hereby corrected as shown below:

On the Title Page

Item (72), Line 2:
"Glen Short"
Should read:
--Glenn Short--

Signed and Sealed this
Tenth Day of June, 2025

Coke Morgan Stewart
*Acting Director of the United States Patent and Trademark Office*